United States Patent
Dey et al.

(10) Patent No.: US 9,874,575 B2
(45) Date of Patent: Jan. 23, 2018

(54) ANALYSIS OF ESTRADIOL AND ANALYTES WITH PHENOLIC OH USING LABELING CHEMISTRY AND LC-MSMS WORKFLOW

(71) Applicant: DH Technologies Development Pte. Ltd.

(72) Inventors: Subhakar Dey, Lexington, MA (US); Subhasish Purkayastha, Acton, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 735 days.

(21) Appl. No.: 14/367,230

(22) PCT Filed: Jan. 16, 2013

(86) PCT No.: PCT/IB2013/000055
§ 371 (c)(1),
(2) Date: Jun. 19, 2014

(87) PCT Pub. No.: WO2013/108113
PCT Pub. Date: Jul. 25, 2013

(65) Prior Publication Data
US 2015/0051111 A1 Feb. 19, 2015

Related U.S. Application Data

(60) Provisional application No. 61/588,902, filed on Jan. 20, 2012.

(51) Int. Cl.
*G01N 33/74* (2006.01)
*G01N 33/58* (2006.01)
G01N 30/72 (2006.01)

(52) U.S. Cl.
CPC .......... *G01N 33/743* (2013.01); *G01N 33/58* (2013.01); *G01N 30/7233* (2013.01); *G01N 2560/00* (2013.01); *Y10T 436/18* (2015.01); *Y10T 436/200833* (2015.01); *Y10T 436/203332* (2015.01)

(58) Field of Classification Search
CPC ........ G01N 1/50; G01N 27/3271; G01N 1/38; G01N 33/491; G01N 33/66; G01N 35/00069; G01N 2035/00158; G01N 2035/0257; B01L 3/50273; B01L 2300/0867; B01L 2300/0806; B01L 2400/0405; B01L 2400/0688

See application file for complete search history.

(56) References Cited

U.S. PATENT DOCUMENTS

| | | | |
|---|---|---|---|
| 2005/0130121 | A1 | 6/2005 | Chong Conklin et al. |
| 2011/0003395 | A1 | 1/2011 | Subhakar et al. |
| 2011/0212534 | A1 | 9/2011 | Taylor et al. |

FOREIGN PATENT DOCUMENTS

| | | |
|---|---|---|
| WO | 2004070352 | 8/2004 |
| WO | 2011-091338 | 7/2011 |

OTHER PUBLICATIONS

Houdier, Stephan et al. "A new fluorescent probe for sensitive detection of carbonyl compounds: sensitivity improvement and application to environmental water samples." Analytical Chimica Acta (2000) 412 221-233.*
Shimada, Kazutake et al. "Development of analyses of biological steroids using chromatography—special reference to vitamin D compounds and neurosteroids." Chromatography (2003) 24 1-6.*
International Search Report from International Patent Application No. PCT/IB2013/00055, dated May 9, 2013.

* cited by examiner

*Primary Examiner* — Christopher Adam Hixson

(57) ABSTRACT

A method is described for mass spectrometric analysis of a sample comprising phenolic OH, such as a steroid comprising a phenolic OH, using a quaternary amino oxy Cookson (QAOC) reagent. The QAOC reagent can improve ionization and fragmentation properties of phenolic OH samples, which can thereby improve quantitation and identification. The method can include derivatizing the phenolic OH sample with the QAOC reagent to create an adduct and analyzing the adduct using mass spectrometry. Derivatization of the sample can be a one-step reaction where the QAOC reagent comprises an aminooxy MS tag or can be a multi-step reaction, where the adduct is formed by the reaction of carbonyl substituted PTAD based reagent and the sample followed by combination with an aminooxy MS tag. The sample can also be enriched prior to reacting it with the reagent. The method can also allow for multiplexing.

18 Claims, 7 Drawing Sheets

• = $^{13}C$ enriched center

ANALYSIS OF ESTRADIOL AND ANALYTES WITH PHENOLIC OH USING LABELING CHEMISTRY AND LC-MSMS WORKFLOW

RELATED U.S. APPLICATIONS

This application claims the benefit of priority from U.S. Provisional Application Ser. No. 61/588,902, the entire teachings of which are incorporated by reference herein.

FIELD

The present teachings relate to the fields of mass spectrometry and tagging reagents useful for mass spectrometry.

BACKGROUND

Labeling chemistry is generally used to improve a mass spectrometry signal.

Conjugation using an aqueous ene-type reaction to derivatize tyrosine using the reagent 4-phenyl-3H-1,2,4-triazole-3,5(4H)-dione (commonly known as PTAD or Cookson Reagent) can provide a particularly useful conjugate for the synthesis of bispecific antibodies (Hitoshi Ban, Jilia Gavrilyuk, Carlos F. Barbas, J. Am. Chem. Soc. 2010, 132, 1523-1525). PTAD has also been used for conjugation with Vitamin D class of compounds for mass spectrometry analysis (Kazutake Shimada, Tomoyuki Oe, Tatsuhito Mizuguchi, Analyst, 1991, 116, 1393-1397).

Quaternary amino oxy Cookson ("QAOC"), a reagent having the same reactive core as PTAD, was developed for the analysis of Vitamin D3 metabolites, as described in U.S. Pub. Pat. Appl. 2011/0212534, which is incorporated by reference herein in its entirety. This reagent was found to react with the conjugated diene functionalities of Vitamin D3 to provide improved ionizing and fragmentation properties for mass spectrometry (MS) analysis of Vitamin D3.

The accurate analysis and quantification of hormones and other compounds containing phenolic OH is becoming increasingly important. For example, estrogen and estrogen-like compounds are playing an ever-increasing role in today's society through hormone replacement therapy. Also, the analysis and quantification of estrogen and estrogen-like compounds helps in the management of estrogen-related diseases, like breast cancer.

However, a need still exists for labels for improved mass spectrometry analysis of compounds containing phenolic OH, such as steroids or estrogens. Analysis of these compounds, which can include hormones such as estradiol, by mass spectrometry has conventionally been difficult. For example, many of these compounds do not contain ionizable groups. Thus, the quantitation of these molecules, e.g. estradiol, in a biological matrix, especially at low concentrations, can be difficult.

While reagents such as pentafluorobenzylbromide and dansyl chloride are commonly used in derivatization strategies for estradiol analysis using mass spectrometry, current strategies involving LC/MSMS for exploiting such derivatization of analytes containing phenolic OH fails to achieve the limit of detection required for clinical assays (Shimada, et.al., Analyst, 116, 1393-1397 (1991); Higashi et al., Chem. Pharm. Bull., 54(11), 1479-1485 (2006)). A need exists for a method of quantitating these analytes that overcomes these drawbacks.

SUMMARY

According to various embodiments, the present teachings provide methods for quantifying compounds having one or more phenolic OH moiety, and metabolites thereof, herein collectively referred to as phenolic OH analytes.

According to various embodiments, a method for mass spectrometric analysis of phenolic OH analytes is disclosed, which can comprise labeling the analytes with a QAOC reagent to generate an adduct and analyzing the adduct using mass spectrometry (MS). In some embodiments, the adduct can be identified and quantitated using LC-MSMS. In some embodiments, the adduct can be analyzed using LC-MSMS and a Multiple Reaction Monitoring (MRM) workflow. In some embodiments, the adduct can have distinct retention times on a reversed phase column, and distinct masses. In some embodiments, under high energy collisions, reporter groups can be generated. In some embodiments, the intensity or the peak area detected for each reporter group can be used not only for identification, but also for quantitation. According to various embodiments, the method can also comprise sample enrichment, e.g., prior to labeling the analytes with a QAOC reagent.

In some embodiments, the adduct can be analyzed using parent daughter ion transition monitoring (PDITM), e.g., using a triple quadrupole MS platform.

In some embodiments, multiple different analytes having phenolic OH groups that have been labeled with a QAOC reagent can be concurrently analyzed using mass spectrometry. For example, different QAOC reagents can be utilized to label different analytes, and the labeled analytes can be analyzed using mass spectrometry, e.g., LC-MSMS. In some embodiments, the QAOC reagent contains one or more isotopically labeled atoms.

According to various embodiments, phenolic OH analytes can be steroids and estrogens. For example, a phenolic OH analyte can be an estrogen compound, such as estrone (E1), estrone sulfate (E1s), 17α-estradiol (E2a), 17β-estradiol (E2b), estradiol sulfate (E2s), equilin (EQ), 17α-dihydroequilin (EQa), 17β-dihydroequilin (EQa), Eqilenin (EN), 17α-dihydroequilenin (ENa) 17β-dihydroequilenin (ENb), Δ8,9-dehydroestrone (dE1), Δ8,9-dehydroestrone sulfate (dE1s) estriol, 16-epiestriol, 17-epiestriol, and 16,17-epiestriol.

In some embodiments, a carbonyl substituted phenyl-3H-1,2,4-triazole-3,5(4H)-dione (carbonyl-PTAD) based reagent can be coupled to an aminooxy tagging agent prior to labeling a phenolic OH analyte (this process is herein referred to as a one-step labeling reaction). In other embodiments, a carbonyl substituted PTAD based reagent without an aminooxy tagging agent can be reacted with a phenolic OH analyte to label the analyte. The labeled analyte can then be mass analyzed. Alternatively, the labeled analyte can be tagged with an aminooxy tag at its carbonyl portion prior to mass analysis (this process is herein referred to as a two-step labeling reaction).

A QAOC reagent can be described by the formula:

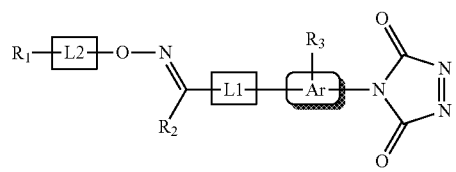

wherein $R_1$ is

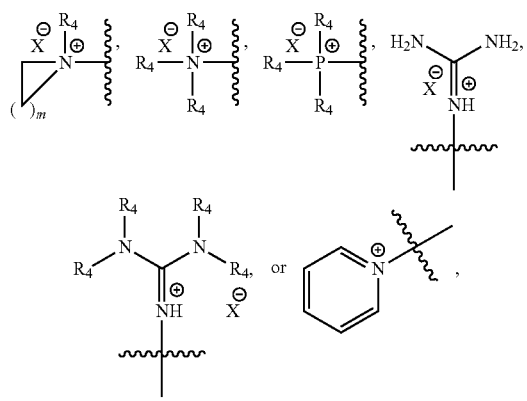

or wherein $R_1$ is:

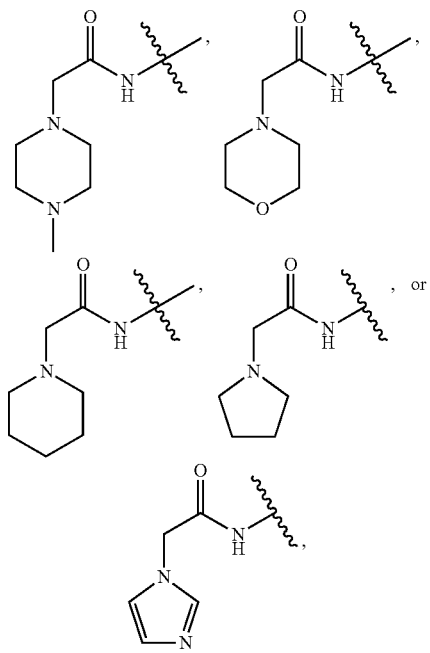

$R_2$ is a cyclic, branched or straight chain, substituted or unsubstituted $C_1$-$C_{18}$ alkyl, $C_1$-$C_{18}$ alkene, or $C_1$-$C_{18}$ alkyne, or a substituted or unsubstituted aromatic group;

$R_3$ is absent or is one or more substituents that are the same or different, which is a cyclic, branched or straight chain $C_1$-$C_{18}$ alkyl, $C_1$-$C_{18}$ alkene, or $C_1$-$C_{18}$ alkyne; halogen (e.g., Cl, Br, I, or F); —$NO_2$, substituted or unsubstituted aromatic (aryl) group; protected or unprotected amino, acyl, carboxylic, or thiol group; —$SO_3H$, —$PO_4^-$, thioether, ether, epoxide, thio-epoxide, azide or aziridine;

each $R_4$ is independently H or a cyclic, branched or straight chain $C_1$-$C_{18}$ alkyl, $C_1$-$C_{18}$ alkene, or $C_1$-$C_{18}$ alkyne;

m is an integer between 1 and 20;

X is an anion;

L1 and L2 are independently bonds or linkers; and

Ar is a bond, an aryl or heteroaryl group.

In some embodiments, Ar is an aryl. In some embodiments, Ar is a phenyl or naphthyl group. In some embodiments, L1 and L2 are independently a bond, a peptide, an oligomer, PEG, $C_1$-$C_{20}$ alkylene chain, $C_1$-$C_6$ alkylene chain, or $C_2$-$C_4$ alkylene chain. In some embodiments, X is a perfluorocarboxylate. In some embodiments, X is $CF_3COO$—, $CF_3CF_2COO$—, $CF_3CF_2CF_2COO$—, $CF_3SO_3COO$, or $(C_6H_5)_4B$—.

In some embodiments, the QAOC reagent can be described by the formula:

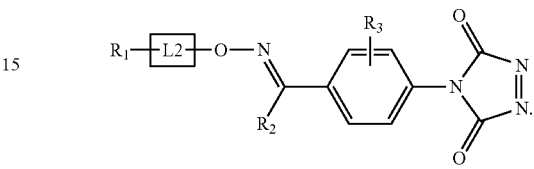

In some embodiments, the QAOC reagent can comprise an aminooxy tagging agent, for example, the QAOC reagent used in a one-step labeling reaction can have the above structure wherein L2 is a $C_1$-$C_{20}$ alkylene group.

In some embodiments, in either of the above structures, $R_2$ is a methyl or ethyl. In some embodiments, $R_3$ is absent. In some embodiments, $R_4$ is a methyl. In some embodiments, m is an integer between 1 and 6 or an integer between 1 and 3. In some embodiments, n is an integer between 1 and 10, an integer between 1 and 5, or an integer between 2 and 4. In some embodiments, X is a perfluorocarboxylate. In some embodiments, X is $CF_3COO$—, $CF_3CF_2COO$—, $CF_3CF_2CF_2COO$—, $CF_3SO_3COO$, or $(C_6H_5)_4B$—.

In some embodiments, the QAOC reagent is the compound:

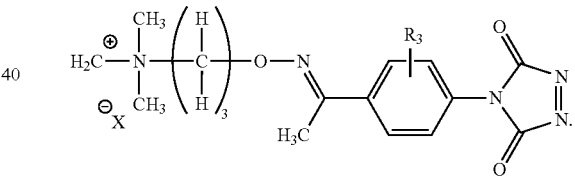

In further aspects, a method for identifying and quantitating one or more phenolic OH analytes in a sample is disclosed, which comprises treating the sample with a QAOC reagent to label one or more phenolic OH analytes, if any, in the sample. The treated sample can then be analyzed by mass spectrometry to identify and quantitate the one or more phenolic OH analytes. For example, the treated sample can be subjected to LC-MSMS analysis for identification and quantitation of the one or more phenolic OH analytes.

In some embodiments, the sample is a biological sample, such as, blood, plasma, serum, urine or saliva. Further, in some embodiments, the phenolic OH analyte is a steroid or estrogen, e.g., estrone (E1), estrone sulfate (E1s), 17α-estradiol (E2a), 17β-estradiol (E2b), estradiol sulfate (E2s), equilin (EQ), 17α-dihydroequilin (EQa), 17β-dihydroequilin (EQb), Eqilenin (EN), 17α-dihydroequilenin (ENa) 17β-dihydroequilenin (ENb), Δ8,9-dehydroestrone (dE1), Δ8,9-dehydroestrone sulfate (dE1s) estriol, 16-epiestriol, 17-epiestriol, and 16,17-epiestriol. In some embodiments in the above method, the phenolic OH analyte is a steroid, and the method further comprises: creating a set of calibration matrices by spiking known volumes of a phenolic OH analyte-depleted biological sample with known amount of one or more phenolic OH internal standard and one or more phenolic OH analyte having known incremental concentrations; treating the samples obtained from step (a) with a QAOC reagent so as to label at least one phenolic OH analyte and corresponding internal standard; analyzing the calibration matrices of step (b) using LC-MSMS; generating a calibration curve using the data obtained from the analysis of step (c); spiking said phenolic OH analyte in the sample with known amount of one or more phenolic OH internal standard; and using said calibration curve to estimate the amount of said at least one phenolic OH analyte which can be a steroid in sample. In some embodiments, the method can further comprises steps of performing sample preparations, either to enrich or clean up the phenolic OH analytes and the one or more phenolic OH internal standard in the calibration matrices.

In some embodiments, in the above method, an internal or external standard comprising a known concentration of the analyte comprising a phenolic OH, such as a steroid analyte comprising a phenolic OH, is treated with a QAOC reagent so as to label at least one phenolic OH analyte in the standard to create a phenolic QAOC standard. The standard and the analyte can then be analyzed, e.g., by liquid chromatography (LC)/mass spectroscopy (MS). They can be analyzed as a mixture or analyzed separately. A calibration curve can be generated from the data obtained from analysis of the phenolic QAOC standard and the amount of said at least one phenolic OH analyte (e.g., a steroid in the sample) can be estimated. For a mixture of the standard and analyte, the mixture can, for example, be subjected to LC separation to elute the labeled standard adduct and the labeled analyte at separate times due to different retention times on the LC column. Each eluant can then be analyzed by mass spectrometry. For example, parent daughter ion transition monitoring (PDITM) can be employed. The ratio of the signal intensity of peak area of the reporter signals generated from the labeled standard relative to the labeled sample can provide relative concentration of the labeled analytes in the sample. As the concentration of the labeled standard adduct is known, the specific concentrations of the labeled analytes in the sample can be determined.

In some embodiments, standards comprising a known concentration of one or more selected phenolic OH analytes can be labeled with a QAOC reagent to form one or more standard adducts. For example, the standard adducts can be generated either by the one-step or the two-step labeling reaction discussed above. The standard adducts can be analyzed using mass spectrometry and then the data obtained from this analysis can be compared to the data obtained from analyzing a sample reacted with a QAOC reagent to label its phenolic OH analytes, if any, to determine the specific concentrations of the phenolic OH analyte(s) of the sample.

In further aspects, a kit is provided that comprises a QAOC reagent and one or more standards comprising known concentrations of a selected phenolic OH analytes labeled with the QAOC reagent.

In further aspects, a kit is provided that comprises a QAOC reagent and one or more standards comprising known concentrations of a selected phenolic OH analytes.

In some embodiments, phenolic OH analytes and vitamin D can be analyzed concurrently. For example, a sample containing phenolic OH analytes and vitamin D can be treated with a QOAC reagent to label the phenolic OH analytes and the vitamin D. The labeled sample can then be analyzed, e.g., in a single run of an LC/MSMS spectrometer, to quantitate both the phenolic OH analytes and the vitamin D.

In some embodiments, a two-step labeling reaction can be provided that allows for multiplexing capability. For example, in some embodiments, different phenolic OH analytes can be labeled with different QAOC reagents. In other embodiments, different phenolic OH analytes can be labeled with a single QAOC reagent and the resulting adducts can be reacted with different aminooxy tags.

BRIEF DESCRIPTION OF THE DRAWINGS

The present teachings will be more fully understood with reference to the appended drawings. The drawings are intended to illustrate, not limit, the present teachings.

Figure 1:
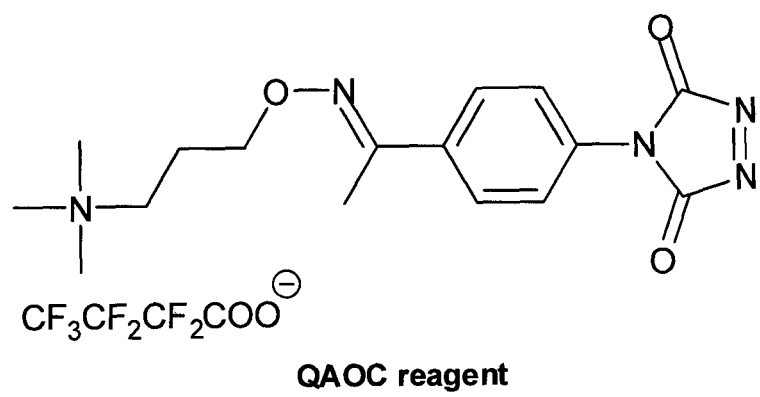
FIG. 1 is one embodiment of a QAOC reagent according to an embodiment of the applicants' teachings.

A detailed description of various embodiments is provided herein below with reference, by way of example, to the following drawings. It will be understood that the drawings are exemplary only and that all reference to the drawings is made for the purpose of illustration only, and is not intended to limit the scope of the embodiments described herein below in any way. For convenience, reference numerals may also be repeated (with or without an offset) throughout the figures to indicate analogous components or features.

DETAILED DESCRIPTION OF VARIOUS EMBODIMENTS

It will be appreciated that for clarity, the following discussion will explicate various aspects of embodiments of the applicants' teachings, but omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments may not require certain of the specifically described details in every implementation, which are set forth herein only to provide a thorough understanding of the embodiments. Similarly it will be apparent that the described embodiments may be susceptible to slight alteration or variation according to common general knowledge without departing from the scope of the disclosure. Aspects of the applicants' teachings may be further understood in light of the following examples and description of various embodiments, which should not be construed as limiting the scope of the applicants' teachings in any way.

According to various embodiments, a method for quantitating an analyte containing phenolic OH, such as estrogen, with a QAOC reagent is provided. In some embodiments, the method can comprise sample enrichment, derivatization, and LC-MSMS analysis. The sample can comprise one or more phenolic OH analytes or metabolites thereof. According to various embodiments, the sample can comprise a plurality of different phenolic OH analytes, and the labeling can comprise labeling each analyte with a different QAOC reagent.

Phenolic OH analytes contain a phenol group:

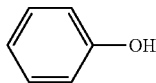

In some embodiments, a phenolic OH analyte can be neutral. In some embodiments, the phenolic OH analyte is an ion. In certain embodiments, a phenolic OH analyte can have a molecular weight in the range of about 50 1000 g/mol. In some embodiments, the phenolic OH analyte can have a molecular weight in the range of about 100-400 g/mol. In some embodiments, the phenolic OH analyte has 2, 3, or more phenolic OH moieties.

In some embodiments, a sample under analysis can contain one or more phenolic OH analytes or metabolites thereof. By way of example, according to various embodiments, the sample can comprise one or more steroids, steroid-like compounds, estrogen, estrogen-like compounds, estrone (E1), estradiol (E2), 17α-estradiol, 17β-estradiol, estriol (E3), 16-epiestriol, 17-epiestriol, and 16,17-epiestriol, and/or metabolites thereof. In various embodiments, the metabolites can be, for example, estriol, 16-epiestriol (16-epiE3), 17-epiestriol (17-epiE3), 16,17-epiestriol (16,17-epiE3), 16-ketoestradiol (16-ketoE2), 16α-hydroxyestrone (16α-OHE1), 2-methoxyestrone (2-MeOE1), 4-methoxyestrone (4-MeOE1), 2-hydroxyestrone-3-methyl ether (3-MeOE1), 2-methoxyestradiol (2-MeOE2), 4-methoxyestradiol (4-MeOE2), 2-hydroxyestrone (2OHE1), 4-hydroxyestrone (4-OHE1), 2-hydroxyestradiol (2-OHE2), estrone (E1), estrone sulfate (E1s), 17α-estradiol (E2a), 17β-estradiol (E2b), estradiol sulfate (E2s), equilin (EQ), 17α-dihydroequilin (EQa), 17β-dihydroequilin (EQb), Eqilenin (EN), 17α-dihydroequilenin (ENa) 17β-dihydroequilenin (ENb), Δ8,9-dehydroestrone (dE1), Δ8,9-dehydroestrone sulfate (dE1s). In some embodiments, the phenolic OH analyte can be a steroid or a steroid-like compound having an A-ring which is sp² hybridized and an OH group at the 3-position of the A-ring.

According to various embodiments, a one-step labeling reaction can be employed to label a phenolic OH analyte. For example, the method can comprise reacting an QAOC reagent having one of the following structures with the phenolic OH group of the analyte, where the QAOC reagent is described by the formula:

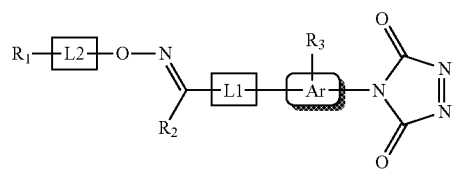

wherein $R_1$ is

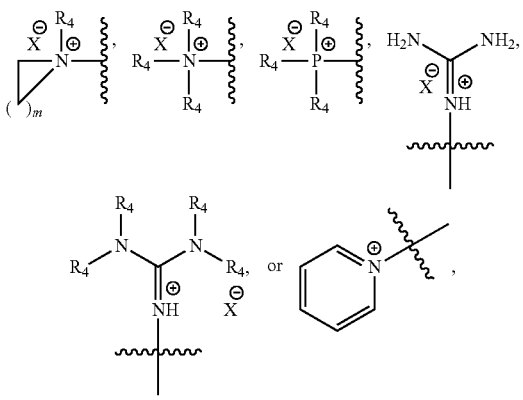

or wherein $R_1$ is:

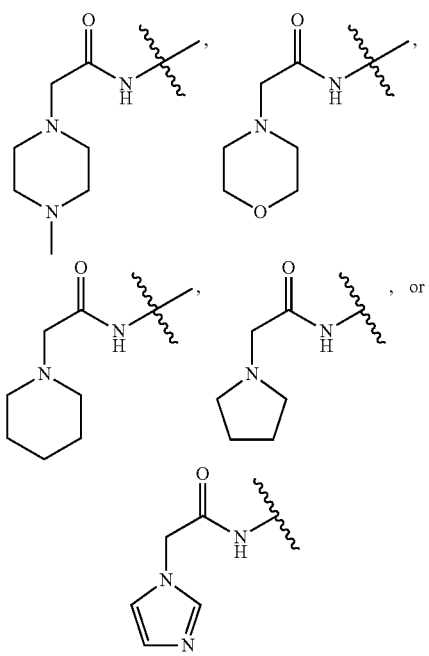

R₂ is a cyclic, branched or straight chain, substituted or unsubstituted $C_1$-$C_{18}$ alkyl, $C_1$-$C_{18}$ alkene, or $C_1$-$C_{18}$ alkyne or a substituted or unsubstituted aromatic group;

R₃ is absent or is one or more substituents that are the same or different, which is a cyclic, branched or straight chain $C_1$-$C_{18}$ alkyl, $C_1$-$C_{18}$ alkene, or $C_1$-$C_{18}$ alkyne; halogen (e.g., Cl, Br, I, or F); —NO₂, substituted or unsubstituted aromatic (aryl) group; protected or unprotected amino, acyl, carboxylic, or thiol group; —SO₃H, —PO₄⁻, thioether, ether, epoxide, thio-epoxide, azide or aziridine;

each R₄ is independently H or a cyclic, branched or straight chain $C_1$-$C_{18}$ alkyl, $C_1$-$C_{18}$ alkene, or $C_1$-$C_{18}$ alkyne;

m is an integer between 1 and 20;

X is an anion;

L1 and L2 are independently bonds or linkers; and

Ar is bond, an aryl or heteroaryl group.

The term "aryl" means, unless otherwise stated, a substituted or unsubstituted polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Aryl" and "heteroaryl" also encompass ring systems in which one or more non-aromatic ring systems are fused, or otherwise bound, to an aryl or heteroaryl system.

The term linker" or "linking agent" refers to a bi-functional moiety (such as an alkylene chain, a peptide, a monomer, an oligomer, or a polymer) that connects two molecules. Non limiting examples of linkers are alkyl chains, polyethylene glycols (PEGs), and peptide or petidomemetic chains.

In some embodiments, Ar is an aryl. In some embodiments, Ar is a phenyl or naphthyl group.

In some embodiments, L1 and L2 are independently a bond, a peptide, an oligomer, PEG, $C_1$-$C_{20}$ alkylene chain, $C_1$-$C_6$ alkylene chain, or $C_2$-$C_4$ alkylene chain. In some embodiments, L1 and L2 are independently a bond, a peptide, $C_1$-$C_6$ alkylene chain, or $C_2$-$C_4$ alkylene chain.

In some embodiments, R₂ is a methyl or ethyl. In some embodiments, R₃ is absent or is a $C_1$-$C_8$ alkyl (branched or straight chain), halo, NO₂, amino, acyl, or carboxylic group. In some embodiments, R₃ is absent. In some embodiments each R₄ is independently H or a $C_1$-$C_{10}$ alkyl which is branched or straight chain, or each R₄ is independently H or a $C_1$-$C_6$ alkyl which is branched or straight chain. In some embodiments, each R₄ is the same. In some embodiments, R₄ is a methyl. In some embodiments, m is an integer between 1 and 6 or an integer between 1 and 3. In some embodiments, X is a perfluorocarboxylate. In some embodiments, X is CF₃COO—, CF₃CF₂COO—, CF₃CF₂CF₂COO—, CF₃SO₃COO, or (C₆H₅)₄B—.

In some embodiments, the QAOC reagent can be described by the formula:

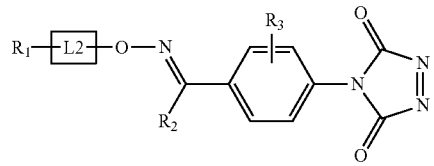

or by the formula:

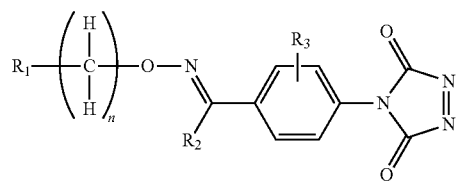

wherein R₁ is;

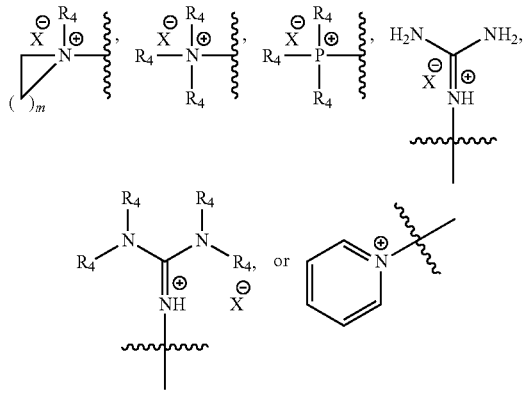

or wherein R₁ is:

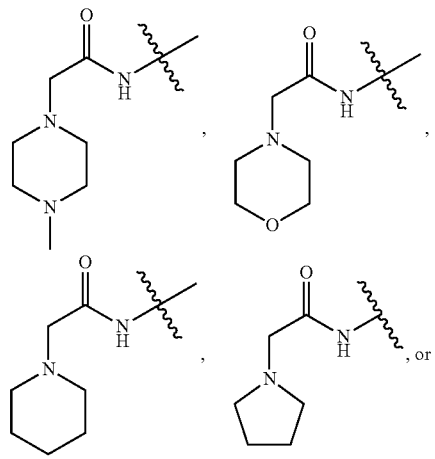

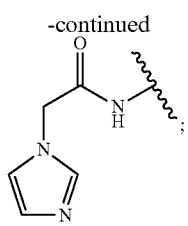

$R_2$ is a cyclic, branched or straight chain, substituted or unsubstituted $C_1$-$C_{18}$ alkyl, $C_1$-$C_{18}$ alkene, or $C_1$-$C_{18}$ alkyne or a substituted or unsubstituted aromatic group;

$R_3$ is absent or is one or more substituents that are the same or different, which is a cyclic, branched or straight chain $C_1$-$C_{18}$ alkyl, $C_1$-$C_{18}$ alkene, or $C_1$-$C_{18}$ alkyne; halogen (e.g., Cl, Br, I, or F); —$NO_2$, a substituted or unsubstituted aromatic (aryl) group; a protected or unprotected amino, acyl, carboxylic, or thiol group; —$SO_3H$, —$PO_4^-$, thioether, ether, epoxide, thio-epoxide, azide or aziridine;

each $R_4$ is independently H or a cyclic, branched or straight chain $C_1$-$C_{18}$ alkyl, $C_1$-$C_{18}$ alkene, or $C_1$-$C_{18}$ alkyne;

m and n are independently integers between 1 and 20;

X is an anion;

L2 is a bond or a linker, and

Ar is absent, an aryl or heteroaryl group.

In some embodiments, in the above structures, $R_2$ is methyl or ethyl. In some embodiments, $R_3$ is absent. In some embodiments, $R_4$ is methyl. In some embodiments, L2 is a bond, a peptide, an oligomer, PEG, $C_1$-$C_{20}$ alkylene chain, $C_1$-$C_6$ alkylene chain, or $C_2$-$C_4$ alkylene chain. In some embodiments, m is an integer between 1 and 6 or an integer between 1 and 3. In some embodiments, n is an integer between 1 and 10, an integer between 1 and 5, or an integer between 2 and 4. In some embodiments, X is a perfluorocarboxylate anion. In some embodiments, X is $CF_3COO$—, $CF_3CF_2COO$—, $CF_3CF_2CF_2COO$—, $CF_3SO_3COO$— or $(C_6H_5)_4B$—.

According to various embodiments, a phenolic OH analyte can be labeled via a two-step labeling reaction, where the aromatic ring of the phenolic OH group is initially reacted with a carbonyl substituted PTAD based reagent that does not contain an aminooxy tagging agent, to form an adduct, and subsequently the adduct is tagged with an aminooxy tagging agent to form a tagged adduct For example, according to various embodiments, the two-step labeling reaction can include reacting a phenolic OH group with a carbonyl substituted PTAD based reagent having the following structure:

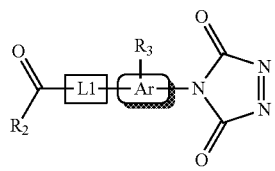

wherein $R_2$ is a cyclic, branched or straight chain, substituted or unsubstituted $C_1$-$C_{18}$ alkyl, $C_1$-$C_{18}$ alkene, or $C_1$-$C_{18}$ alkyne or a substituted or unsubstituted aromatic group;

$R_3$ is absent or is one or more substituents that are the same or different, which is a cyclic, branched or straight chain $C_1$-$C_{18}$ alkyl, $C_1$-$C_{18}$ alkene, or $C_1$-$C_{18}$ alkyne; halogen (e.g., Cl, Br, I, or F); —$NO_2$, a substituted or unsubstituted aromatic (aryl) group; a protected or unprotected amino, acyl, carboxylic acid, or thiol group; —$SO_3H$, thioether, ether, epoxide, thio-epoxide, azide or aziridine;

Ar is a bond, an aryl group, or a heteroaryl group; and

L1 is a bond or linker.

In some embodiments, Ar is an aryl. In some embodiments, Aryl is a phenyl or naphthyl group. In some embodiments, L1 is a bond, a peptide, an oligomer, PEG, $C_1$-$C_{20}$ alkylene chain, $C_1$-$C_6$ alkylene chain, or $C_2$-$C_4$ alkylene chain. In some embodiments, $R_3$ is absent or is a $C_1$-$C_8$ alkyl, $C_1$-$C_8$ alkene, $C_1$-$C_8$ alkyne, halogen, or —$NO_2$. In some embodiments, $R_3$ is absent. The reaction of the aromatic ring of the phenolic OH group with the above carbonyl substituted PTAD based reagent can create an adduct containing the substructure:

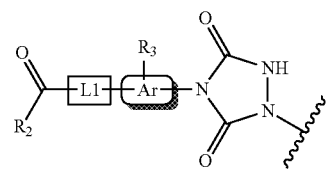

The adduct can then be reacted with an aminooxy tag such as the tag having the structure:

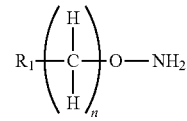

wherein n is from 1 to 20, from 1-15, from 1 to 10, from 1 to 5, or from 2 to 4 and $R_1$ is a quaternary amine or a substituent having the structure:

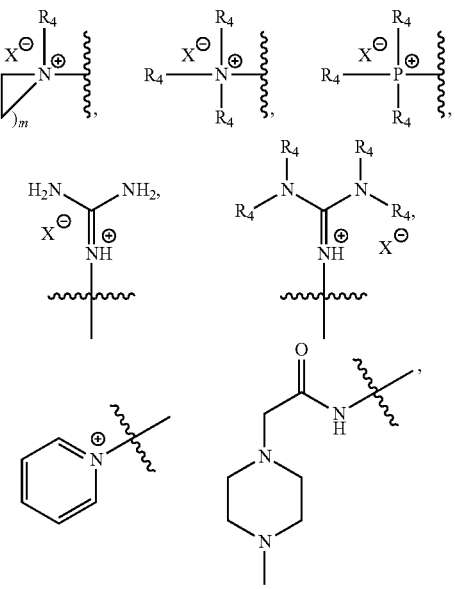

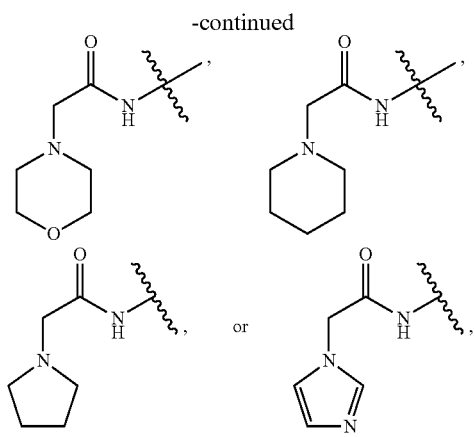

wherein each $R_4$ is independently H or a cyclic, branched or straight chain $C_1$-$C_{18}$ alkyl, $C_1$-$C_{18}$ alkene, or $C_1$-$C_{18}$ alkyne;

m is an integer between 1 and 20, and X is an anion, to form a tagged adduct. The tagged adduct has the substructure:

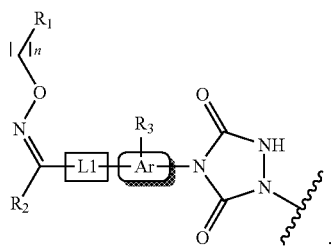

Thus, the two-step reaction, according to various embodiments, comprises treating a phenolic OH sample with a carbonyl substituted PTAD based reagent to create an adduct and reacting the adduct with an aminooxy tag to form a tagged adduct for analysis. In some embodiments, the tagged adduct comprises the substructure:

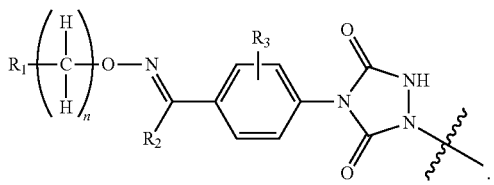

Figure 4:
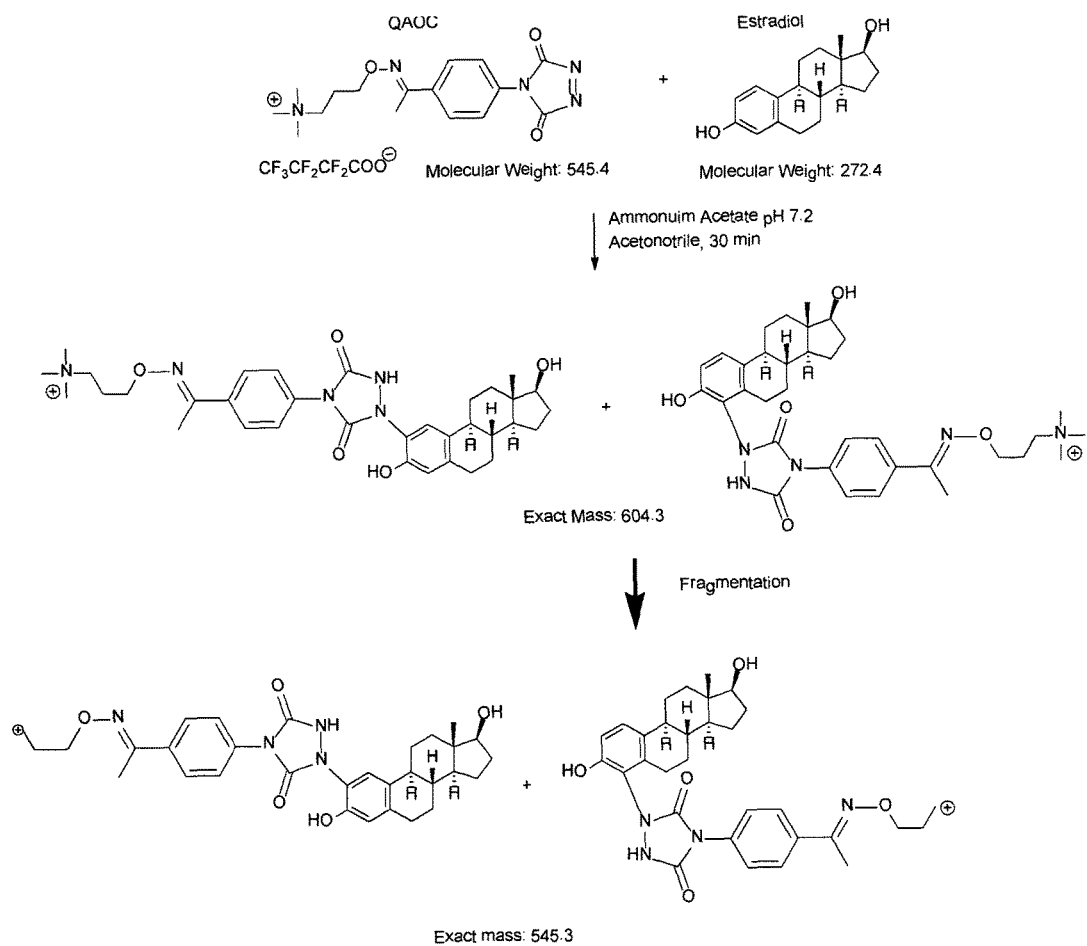
FIG. 4 is a reaction scheme showing reaction of estradiol with QAOC reagent forming two isomeric species of same mass and the fragmentation pattern of those two isomers generating reporter ions according to various embodiments of the present teachings.

FIG. 4 illustrates an exemplary reaction between estradiol and a QAOC reagent. Though the exemplary reaction is a one-step reaction, multi-step reactions, such as two-step reactions, for example, are also possible. In some embodiments, a one-step labeling reaction is used where, for example, a carbonyl substituted PTAD based reagent coupled to an aminooxy MS tag, as illustrated in FIG. 1 (QAOC reagent), is employed to label a phenolic OH analyte. As used herein, the term "aminooxy MS tag" is used interchangeably with "aminooxy tag." In other embodiments, the method comprises first treating a phenolic OH analyte with a carbonyl substituted PTAD based reagent to produce an adduct, and then tagging the adduct with an aminooxy mass spectrometry (MS) tagging agent to form a labeled adduct. As used herein, the term "aminooxy MS tagging agent" is used interchangeably with "aminooxy tagging agent." The labeled adduct can be analyzed using mass spectrometry.

The method can further comprise providing a standard comprising a known phenolic OH analyte, treating the known phenolic OH analyte of the standard with a QAOC reagent to form a standard adduct. In various embodiments, the standard can be treated with a QAOC reagent or a carbonyl substituted PTAD based reagent via a one-step or two-step labeling reaction according to the present teachings to form a standard adduct. The standard adduct can then be mixed with a adduct formed by labeling a phenolic OH analyte with a QAOC reagent or carbonyl substituted PTAD based reagent, followed by reaction with aminooxy MS tag, to form a mixture. The mixture can then be analyzed using mass spectrometry, e.g., using LC-MSMS spectrometry. In some embodiments, a relative concentration of a phenolic OH analyte can be obtained. In other embodiments, absolute quantitation of a phenolic OH analyte can be obtained by using a known concentration of a standard.

According to various embodiments, a method for relative quantitation of one or more phenolic OH analytes can comprise labeling the one or more analytes, followed by analysis using mass spectrometry. According to some embodiments the one or more phenolic OH analytes and/or metabolites thereof can be quantified. According to some embodiments, the aminooxy tagging agents can comprise a set of isobaric tags. According to some embodiments, in a first step, at least one phenolic OH analyte in a standard can be labeled with a carbonyl substituted PTAD based reagent to form a standard adduct. In a second step, the standard adduct can be tagged with a first isobaric tag from a set of isobaric tags. A test sample can be reacted with a carbonyl substituted PTAD based reagent to label one or more phenolic OH analytes, if any, in the test sample. The labeled phenolic OH analytes in the test sample can then be tagged with a second isobaric tag from the same set of isobaric tags, which is different from the first isobaric tag. The labeled standard and the labeled test sample can then be combined and the resulting mixture can be subjected to liquid chromatography (LC) separation on a reversed phase column. The labeled phenolic OH and/or phenolic OH metabolites can have distinct retention times and can elute from the column at separate times. The eluting peaks can comprise peaks containing the labeled analyte and peaks containing the labeled standard. The eluant from the column can subsequently be analyzed using mass spectrometry.

It should be understood that absolute quantitation of phenolic OH analytes, where the standard has a known concentration of a phenolic OH analyte, can be performed in the same manner as described above for relative quantitation. Also, where phenolic OH analytes and/or metabolites of phenolic OH analytes are mentioned above, it should be understood that any phenolic OH analyte can be used.

According to various embodiments, a sample comprising a plurality of different phenolic OH analytes can be treated with different QAOC reagents to label each of two or more of the phenolic OH analytes with a different one of said reagents. The labeled sample can then be analyzed using mass spectrometry, e.g., LC/MSMS, to quantitate the labeled phenolic analytes. In some embodiments, such analysis of the sample can be performed in a single run of the spectrometer. As discussed above, in some embodiments, the phenolic OH analytes can be steroid or steroid-like analytes.

According to various embodiments, samples containing one or more compounds having a phenolic OH may be enriched by various methods prior to analysis. The enrichment method can depend upon the type of sample, such as blood (fresh or dried), plasma, serum, urine, or saliva. Exemplary enrichment methods can comprise, without limitation, protein precipitation, liquid-liquid extraction, solid-liquid extraction, affinity capture/release, antibody mediated enrichment and ultrafiltration. Other enrichment methods, or a combination of two or more enrichment methods may be used. Exemplary sample enrichment processes are provided in Example 1 below.

In some embodiments, the analysis of phenolic OH analytes can comprise generating reporter ions, e.g., via a high-energy collision in a mass spectrometer, and utilizing the intensity or the peak area of the reporter ions for quantitation. By way of example, the QAOC reagents shown above can undergo neutral loss during high energy collisions (MSMS) leaving a charged analyte species as the reporter ion, and the reporter ion can then be subjected to $MS^3$ analysis. In some embodiments, the QAOC reagents can generate a tag fragment upon a high energy collision, and the tag fragment can then be subjected to $MS^3$ analysis.

According to various embodiments, a plurality of mass spectrometry (MS) tagging agents can be used for labeling one or more phenolic OH analytes and/or adducts thereof formed in accordance with the present teachings. According to some embodiments, the aminooxy tagging agents can fragment well to provide intense reporter ions. According to some embodiments, the aminooxy tagging agents can comprise tagging agents that are specifically designed for mass spectrometry and according to some embodiments, the aminooxy tagging agent is specifically designed for a Multiple Reaction Monitoring (MRM) assay. In some embodiments, an aminooxy tagging agent can be used to tag an adduct generated by labeling a phenolic OH analyte. In some embodiments in which a standard adduct is used for quantitation of phenolic OH analytes, an aminooxy tagging agent can be used to tag the standard adduct. In various embodiments, the standard adduct can be used for relative quantitation of analytes as compared to the standard adduct. In some embodiments, where the concentration of the standard adduct is known, the standard adduct can be used for absolute quantitation of analytes. In some embodiments, various aminooxy MS tagging agents can be used to label various analytes. For example, the aminooxy MS tagging agents can be different isobaric tags or different mass differential tags. By way of example, the aminooxy MS tagging agent used to tag the standard adduct can comprise a first isobaric tag from a set of isobaric tags, while the aminooxy MS tagging agent used to tag the adduct from the sample can comprise a second isobaric tag from the same set of isobaric tags, but that differs from the first isobaric tag.

According to some embodiments, at least two different categories of aminooxy tagging agents can be used to generate reporter groups under high energy collisions. The QAOC reagents can be formed by using either a one-step or a two-step tagging reaction using these aminooxy tagging agents combined with a compound having the structure (carbonyl substituted PTAD based reagent):

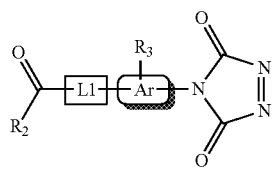

$R_2$ is a cyclic, branched or straight chain, substituted or unsubstituted $C_1$-$C_{18}$ alkyl, $C_1$-$C_{18}$ alkene, or $C_1$-$C_{18}$ alkyne or a substituted or unsubstituted aromatic group;

$R_3$ is absent or is one or more substituents that are the same or different, which is a cyclic, branched or straight chain $C_1$-$C_{18}$ alkyl, $C_1$-$C_{18}$ alkene, or $C_1$-$C_{18}$ alkyne; halogen (e.g., Cl, Br, I, or F); —$NO_2$, a substituted or unsubstituted aromatic (aryl) group; a protected or unprotected amino, acyl, carboxylic acid, or thiol group; —$SO_3H$, thioether, ether, epoxide, thio-epoxide, azide or aziridine;

L1 is a bond or linker; and

Ar is a bond, an aryl or heteroaryl group.

Exemplary compounds from a first and second category or set of aminooxy MS tagging agents which can be used, are shown below.

In the first category, the aminooxy MS tagging agent is: $R_1$—$(CH_2)_n$—$ONH_2$ wherein $R_1$ is a quaternary amine or phosphate or a substituent having a structure such as:

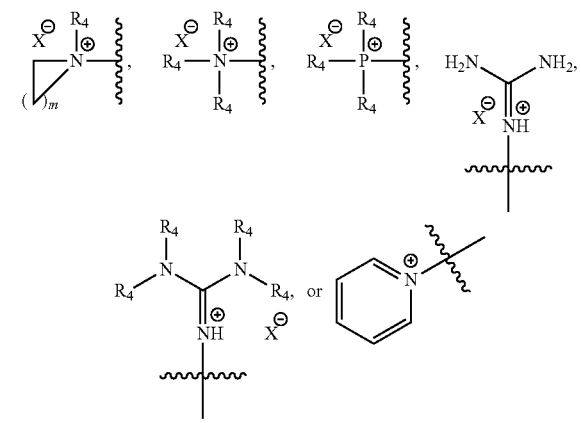

wherein each $R_4$ is independently H or a cyclic, branched or straight chain $C_1$-$C_{18}$ alkyl, $C_1$-$C_{18}$ alkene, or $C_1$-$C_{18}$ alkyne, m is an integer between 1 and 20, from 1 to 15, from 1 to 10, or from 1 to 5, and X is an anion.

In the second category, the aminooxy MS tagging agent is:

$R_1$—$(CH_2)_n$—$ONH_2$ wherein $R_1$ can be, but is not limited to, one or more of these five structures:

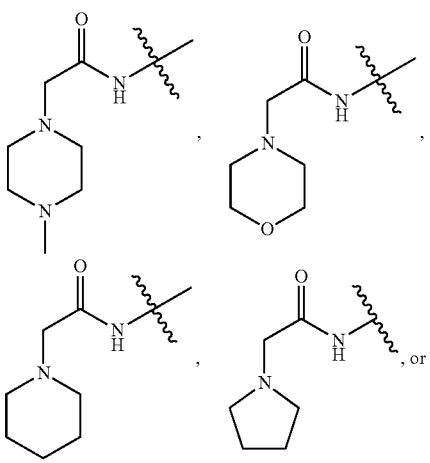

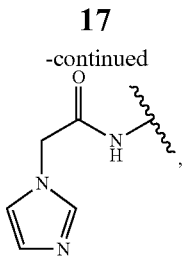

and n can be from 1 to 20, from 1 to 15, from 1 to 10, or from 1 to 5.

An aminooxy MS tagging agent from the first category of aminooxy MS tagging agents can undergo neutral loss during high energy collision (MSMS) leaving a charged analyte species as the reporter ion, which can then be subjected to $MS^3$ analysis. An aminooxy MS tagging agent from the second category of aminooxy MS tagging agents can yield a tag fragment as the reporter ion, on a high energy collision.

As mentioned above, the aminooxy MS tagging agent can be combined with the carbonyl portion of an adduct formed by labeling a phenolic OH analyte with a carbonyl substituted PTAD based reagent—to create a tagged adduct.

Figures 2A, 2B:
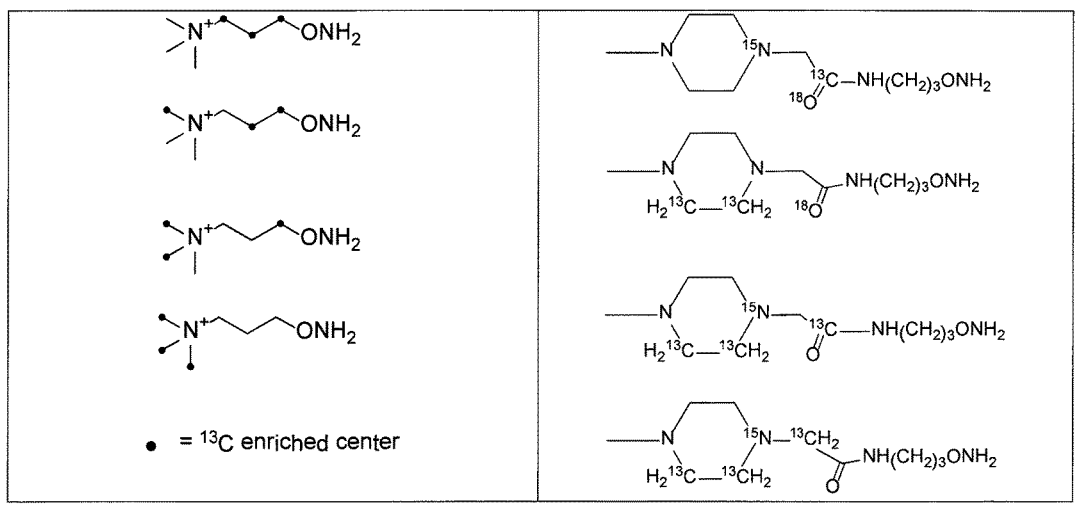
FIG. 2A shows an exemplary set of four aminooxy tagging agents that can be used in a four-plex assay according to various embodiments of the present teachings.
FIG. 2B shows an exemplary set of four aminooxy tagging agents that can be used in a four-plex assay according to various embodiments of the present teachings.

According to various embodiments, for each type of aminooxy MS tagging agent, a plurality of isobaric tagging or mass differential tagging agents can be formulated and used. FIGS. 2A and 2B each respectively depict a set of isobaric 4-plex aminooxy MS tagging agents. Each set of isobaric tagging agents can have identical chemical structures and masses but can comprise different combinations and/or positions of isotopes.

In some embodiments, parent daughter ion transition monitoring (PDITM) of the labeled phenolic OH analytes can be performed using a triple quadrupole MS platform. More details about PDITM and its use are described in U.S. Patent Application Publication No. US 2006/0183238 A1, which is incorporated herein in its entirety by reference. The type of mass spectrometry analysis performed on the labeled phenolic OH analytes as described herein is not limiting. In various embodiments, the LC-MSMS can be employed. In some embodiments, the aminooxy MS tagging agent undergoes neutral loss during MSMS and leaves a reporter ion that is a charged analyte species. In some embodiments, the aminooxy MS tagging agent forms a reporter ion during MSMS that is a tag fragment.

In some embodiments, a method for analysis of a sample containing phenolic OH analytes according to the present teachings can employ internal standards. In some embodiments, such internal standards can be made by reacting the phenolic-OH analytes with one or more isotopic variants of the QAOC labeling reagent. The tagging chemistry and the methodology of the present teachings can provide increased sensitivity relative to known methods, and, in various embodiments, can eliminate the need for $^2H$-containing, $^{13}C$-containing, $^{15}N$-containing, and $^{18}O$-containing standards of phenolic OH analytes. Isotope labeled standards of some phenolic OH analytes are not commercially available, which makes absolute quantitation of these analytes difficult without the present teachings. According to the present teachings, in some embodiments, each analyte can have its own internal standard. The reporter signals can be specific to the standard sample and to the test sample.

In some embodiments, the QAOC reagent used for the labeled standard can comprise a first mass differential tag from a set of mass differential tags. The labeled sample can comprise a second mass differential tag from the same set of mass differential tags, but that differs from the first mass differential tag. The labeled sample can then be analyzed using mass spectrometry, LC-MSMS analysis of the labeled sample, a combination thereof, or the like. According to various embodiments, the method for quantitation of one or more phenolic OH analytes can comprise a two-step chemical reaction to modify the analytes, followed by mass analysis using mass spectrometry. According to various embodiments, the two-step chemical reaction can comprise first derivatizing the aromatic ring of the phenolic OH functionality in a phenolic OH analyte with a carbonyl substituted PTAD based reagent to form an adduct, and then labeling the adduct with an (MS) tagging agent, for example an aminooxy MS tagging agent. According to some embodiments, liquid chromatography-tandem mass spectrometry (LC-MSMS) can be used to analyze the modified analyte. Adducts of different analytes can have different distinct retention times on a reversed phase column, and distinct masses, and can elute from the column at separate times. The eluant from the column can be subjected to MSMS analysis. Under high energy collision, reporter groups can be generated. The intensities or peak areas of the reporter groups can be used for identification and/or quantitation.

Isobaric tags allow for multiplexing and provide a method for multiplexed analysis of phenolic OH analytes, with high throughput and lower cost of analysis per sample. Since there is one common functional group in all of the phenolic OH analytes, in various embodiments, only one tag is needed for each analyte. In some embodiments, using PDITM increases specificity and reduces the risk of error. The reagent design makes it a good tool for FlashQuant™ application and enables $MS^3$ capability which helps in confirming the identity of the analyte.

According to various embodiments, a first isobaric tag from one set of isobaric reagents can be made to contact a standard that can comprise a known phenolic OH analyte, for example, at a known concentration. The contact can be made under conditions that favor a reaction between the first isobaric tag and the standard. A second isobaric tag from the same set of isobaric reagents as the first isobaric tag can be made to contact a sample comprising an unknown concentration of a phenolic OH analyte. As described further below, the tagged analytes of the standard and sample can be mixed together and analyzed to determine the concentration of the analytes in the sample. The analysis can comprise separating the mixture to form separated analytes, and analyzing the separated analytes. Methods of separation that can be used include gas chromatographic methods, liquid chromatographic methods, other chromatographic methods, electrophoretic methods, electroosmotic methods, mass differential separation methods, and the like. In an exemplary embodiment, liquid chromatography is used to separate the various analytes in the mixture and thus form separated analytes.

In some embodiments, chromatographic separation can be performed on a reversed phase column and peaks eluting from the column can be subjected to subsequent analysis. In some embodiments, the subsequent analysis can comprise mass spectrometry or, more particularly, Parent Daughter Ion Transition Monitoring (PDITM). By comparing the results from the PDITM, the concentration of the phenolic OH analyte in the sample can be determined, as is described in more detail below. More details about PDITM and its use can be found in published application US 2006/0183238 A1, which is incorporated herein in its entirety by reference.

Figure 3A:
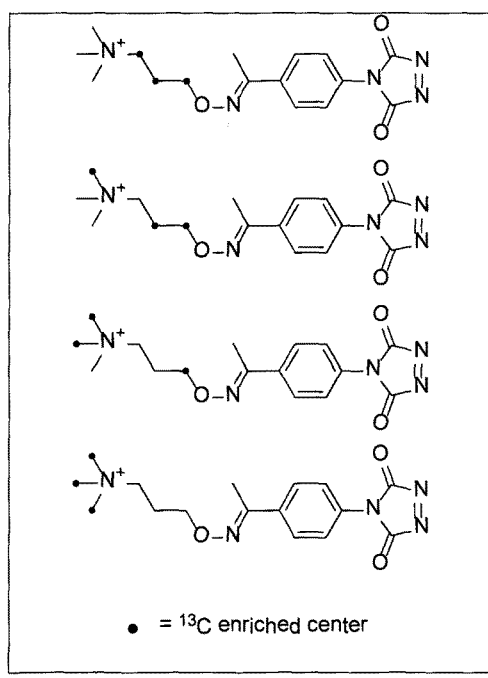
FIG. 3A shows an exemplary set of four mass differential tags comprising four different reagents that can be used in a four-plex assay, according to various embodiments of the present teachings.
Figure 3B:
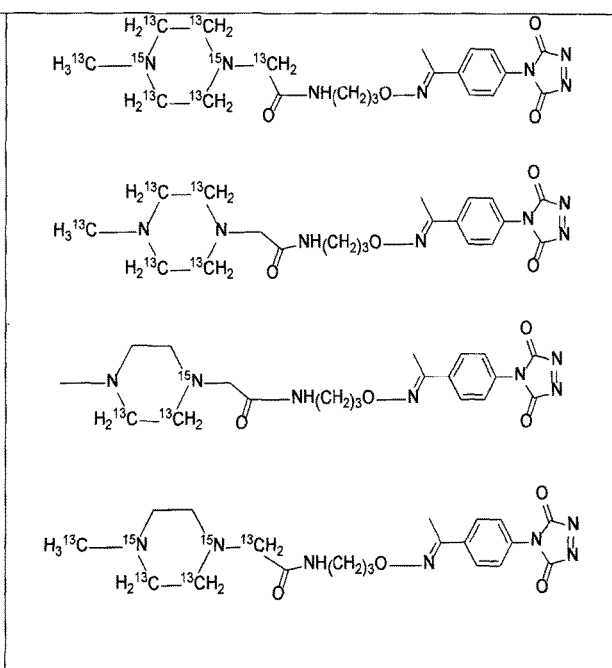
FIG. 3B shows an exemplary set of four mass differential tags comprising four different reagents that can be used in a four-plex assay, according to various embodiments of the present teachings.

According to some embodiments, mass differential tagging agents instead of isobaric tagging reagents, can be used. Exemplary mass differential agent pairs are depicted in FIGS. 3A and 3B. According to various embodiments, the aminooxy MS tagging agents can be used for relative and absolute quantitation in multiplex assays. According to some embodiments, the aminooxy MS tagging agents can be used for two-plex, three-plex, four-plex, and other multi-plex assays.

In some embodiments, the reagent can be reacted with samples containing one or more Vitamin D compound as described in U.S. Pub. Pat. Appl. 2011/0212534, herein incorporated by reference, as well as the phenolic-OH analytes as described herein for multiplex analysis of both classes of compounds.

In some embodiments, the QAOC reagent is combined with the sample at an equimolar concentration of phenolic OH moieties. In some embodiments, an excess (for example, about 10%, about 20%, about a two-fold excess, or about a four-fold excess) of QAOC reagent relative to the phenolic OH moiety is added to the phenolic OH sample. In some embodiments less than an equimolar concentration of QAOC is used, for example, the QAOC concentration may be about 25%, about 50%, or about 75% of the molar concentration of phenolic OH moiety. In some embodiments, the QAOC reagent is combined with the sample at a concentration of between 1 μg/mL-100 mg/mL, or between 100 μg/mL-10 mg/mL in the sample solution.

In some embodiments, the tagging chemistry and the method can be run on any triple quadrupole instruments, for example, those including FlashQuant™ with a MALDI source. Reagent kits, data analysis software, and the MS platform are provided in some embodiments as an analyzer for phenolic OH analytes and their metabolites.

Different liquid chromatography and mass spectrometry methods, systems, and software that can be used in accordance with various embodiments of the present teachings include those described in U.S. Provisional Patent Application No. 61/182,748 filed May 31, 2009, and in U.S. Patent Application No. US 2006/0183238 A1 which published on Aug. 17, 2006. Both of these references are incorporated herein by reference.

According to yet other embodiments of the present teachings, a kit is provided that comprises a QAOC reagent, such as those discussed above. In other embodiments, a kit is provided that comprises a carbonyl substituted PTAD based reagent and one or more aminooxy MS tagging agents. The aminooxy MS tagging agent can comprise compounds from the first and/or second category or set of aminooxy MS tagging agents, described above. In some embodiments, the kit can comprise a standard comprising a known phenolic OH analyte.

According to various embodiments of the present teachings, a kit is provided that can comprise one or more of a carbonyl substituted PTAD based reagent and an aminooxy MS tagging agent. In some embodiments, the kit can comprise a standard containing a known concentration of a steroid analyte comprising phenolic OH.

In some embodiments, the kit can comprise at least one standard comprising a known concentration of a known phenolic OH analyte. According to some embodiments, the aminooxy MS tagging agent can be an isobaric tag from a set of isobaric tags and in some embodiments the kit can include a plurality of different isobaric tags from a set of isobaric tags. According to some embodiments, the aminooxy MS tagging agent can be a mass differential tag from a set of mass differential tags and in some embodiments the kit can include a plurality of different mass differential tags from a set of mass differential tags. According to some embodiments, the kit can comprise a carbonyl substituted PTAD based reagent, an aminooxy MS tagging agent, a standard comprising a known phenolic OH analyte and/or a known concentration of a known phenolic OH analyte, and further can comprise instructions for labeling the phenolic OH analyte.

According to yet other embodiments of the present teachings, the kit can comprise a QAOC reagent as shown in FIG. 1, a different QAOC reagent, a combination thereof, or the like. The kit can also comprise a standard comprising a known phenolic OH analyte. In some embodiments, the standard can comprise a known concentration of a known phenolic OH analyte. In some embodiments, the QAOC reagent included in the kit can comprise one or more isobaric tags from a set of isobaric tags. In some embodiments, the kit can comprise a plurality of different isobaric tags from a set of isobaric tags. In some embodiments, the QAOC reagent included in the kit can comprise one or more mass differential tags from a set of mass differential tags. In some embodiments, the kit can comprise a plurality of different mass differential tags from a set of mass differential tags.

According to various embodiments, the kit can comprise buffers, one or more chromatographic columns, and optionally other reagents and/or components useful in carring out the assay. In some embodiments, the kit can comprise, for example, a homogeneous assay such that the user need only add a sample. In some embodiments, the kit can comprise calibration or normalization reagents or standards. Information pertaining to instrument settings that can or should be used to perform an assay can also be included in the kit. In some embodiments, information pertaining to sample preparation, operating conditions, volumetric amounts, temperature settings, and the like, is included with the kit.

The kit can be packaged in a hermetically sealed container containing one or more reagent vessels and appropriate instructions. An electronic medium can be included in the kit, having stored thereon electronic information pertaining to one or more assays, measurement values, transition pairs, operating instructions, software for carrying out operations, a combination thereof, or the like. According to various embodiments, a method can be provided for the synthesis of the QAOC reagent and its intermediates.

Aspects of the present teachings can be further understood in light of the following examples, which should not be construed as limiting the scope for the present teachings in any way.

EXAMPLES

Example 1

Illustration of the Steps in the Synthesis of a Labeled QAOC Reagent

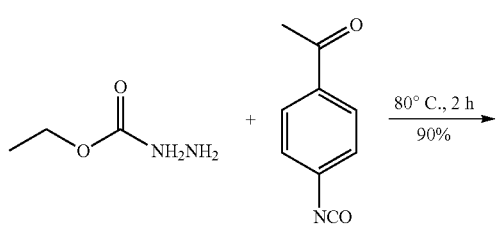

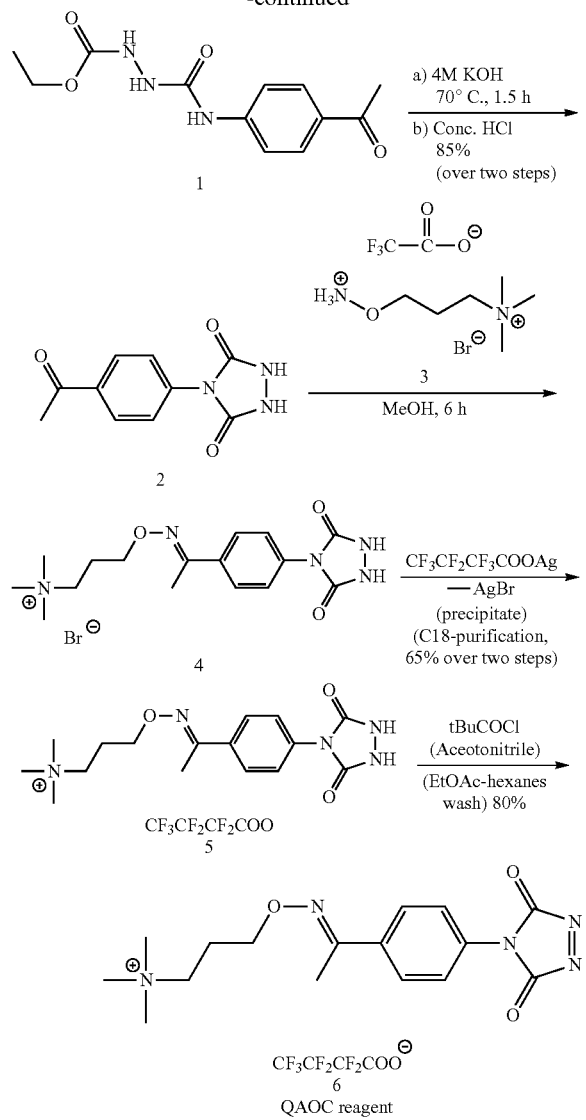

Synthesis of p-Acetyl-4-phenyl-1-carbethoxysemicarbazide (1)

To a solution of ethyl carbazate (6.46 g, 62.05 mmol) in toluene (100 mL) was added dropwise a solution of 4-acetylphenyl isocyanate (10 g, 62.05 mmol) in toluene (250 mL). The reaction mixture was stirred at room temperature for 2 h and then at 80° C. for 2 h. The precipitate formed in the reaction was filtered and dried in vacuum oven to give p-acetyl-4-phenyl-1-carbethoxysemicarbazide 1 (16.5 g, 90%). It was used without further purification in the next reaction step. (Synthesis adopted from: Organic Syntheses, Coll. Vol. 6, p. 936 (1988); Vol. 51, p. 121 (1971). 4-PHENYL-1,2,4-TRIAZOLINE-3,5-DIONE). In various aspects, the values of each of the components used in this example can be increased or decreased by an amount in the range of from about 5% to about 20%, for example, each component can be used in an amount that is from 5% less to 5% more than the value used in this example, each component can be used in an amount that is from 10% less to 10% more than the value used in this example, each component can be used in an amount that is from 15% less to 15% more than the value used in this example, or each component can be used in an amount that is from 20% less to 20% more than the value used in this example. In various aspects, the values can be varied by about plus or minus 5% to 20%.

Synthesis of p-Acetyl-4-phenylurazole (2)

p-Acetyl-4-phenyl-1-carbethoxysemicarbazide 1 (15 g, 56 mmol) was heated with aqueous 4 M KOH solution (28 mL, 112 mmol) at 70° C. for about 2 h. Leftover granular solid was filtered off using a sintered filter funnel. Filtrate was cooled to room temperature and acidified with concentrated HCl. The precipitate formed was filtered and dried in vacuum oven to give p-acetyl-4-phenylurazole 2 as light yellow solid (12.4 g, 85%). $^1$H NMR (400 MHz, DMSO-d6): s=1.65 (s, 3H), 6.70 (d, 2H), 7.10 (d, 2H), 9.50 (s, 2H). (Synthesis adopted from: Organic Syntheses, Coll. Vol. 6, p. 936 (1988); Vol. 51, p. 121 (1971). 4-PHENYL-1,2,4-TRIAZOLINE-3,5-DIONE). In various aspects, the values of each of the components used in this example can be increased or decreased by an amount in the range of from about 5% to about 20%, for example, each component can be used in an amount that is from 5% less to 5% more than the value used in this example, each component can be used in an amount that is from 10% less to 10% more than the value used in this example, each component can be used in an amount that is from 15% less to 15% more than the value used in this example, or each component can be used in an amount that is from 20% less to 20% more than the value used in this example. In various aspects, the values can be varied by about plus or minus 5% to 20%.

Synthesis of p-Acetyl-4-phenylurazole Quaternary Aminooxy Adduct Bromide (4)

A suspension of p-Acetyl-4-phenylurazole 2 (2.10 g, 9.58 mmol) and quaternary aminooxy tag 3 (6.74 g, 20.6 mmol, in 100 mL of methanol-acetic acid (95:5 v/v) (the quaternary aminooxy tag as a labeling reagent is described in published U.S. application, 2011-0003395, incorporated herein in its entirety by reference), was stirred at ambient temperature for 48 h. HPLC analysis at this stage showed 95% conversion of 2 to the product p-Acetyl-4-phenylurazole quaternary aminooxy adduct 4. Column: DeltaPak C18, 3.9.times.150 mm, Buffer A: Water+0.1% TFA, Buffer B: Acetonitrile+0.085% TFA, Wavelength (Signal=254 nm, Reference=360 nm), Flow=1 mL/min. Concentrations of analytes were approximately 0.25 mg/mL in methanol. Retention time of p-Acetyl-4-phenylurazole 2=5.1 min and p-Acetyl-4-phenylurazole quaternary aminooxy adduct 4=5.5 min. ES-MS data: M+ (calculated M+=$C_{16}H_{24}N_5O_3$+=334.19, observed M+=334.20 and 275.50 (-Me$_3$N)). Crude product was isolated as a white solid after removal of methanol. In various aspects, the values of each of the components used in this example can be increased or decreased by an amount in the range of from about 5% to about 20%, for example, each component can be used in an amount that is from 5% less to 5% more than the value used in this example, each component can be used in an amount that is from 10% less to 10% more than the value used in this example, each component can be used in an amount that is from 15% less to 15% more than the value used in this example, or each component can be used in an amount that is from 20% less to 20% more than the value used in this example. In various aspects, the values can be varied by about plus or minus 5% to 20%.

Counter ion exchange: The solid so obtained was dissolved in 40 mL of water and 30 mL (11.50 mmol of 4) of which was used for exchange. To this solution (in a 50 mL Falcon tube) a solution of silver heptafluoro butyrate (3.69 g, 11.53 mmol in 15 mL of deionized water) was added at once and mixed briefly by flipping the tube. Precipitate was separated by centrifugation at 3000 rpm for 2 min. Supernatant checked for any bromide ion (Br$^-$) by addition of a dilute solution of silver heptafluoro butyrate (1 drop). Formation of turbidity indicates presence of Br$^-$. To ensure complete precipitation of bromide ion another 0.2 equivalent (0.738 mg, in 5 mL water) of silver heptafluoro butyrate added, mixed, centrifuged and checked for Br$^-$. A clear solution indicates total consumption of all Br$^-$. Filtrate was taken in a syringe and filtered again through a 5 micron filter (25 mm, Millex LCR, PTEF, 25 mL/filter) and purified by flash chromatography (Purified in two batches: 43 g, C18, Isco column, Flow=40 ml/min, Solvent A: Water, Solvent B: Methanol, column equilibrated with 100 mL 50% B then 250 mL 2% B. Sample was loaded as solution on column, 0-6 min 2% B then 6-35 min 2-85% B, wavelength=254 nm). Fractions containing product were analyzed by analytical HPLC for purity and pure (>95%) fractions were pooled and dried in a rotary evaporator to give p-Acetyl-4-phenylurazole quaternary aminooxy adduct heptafluoro butyrate 5 as white solid. Solid was co-evaporated with 20 mL of toluene and dried under vacuum to ensure complete removal of water. Final yield and HPLC purity was 2.6 g (65%) and >98%. In various aspects, the values of each of the components used in this example can be increased or decreased by an amount in the range of from about 5% to about 20%, for example, each component can be used in an amount that is from 5% less to 5% more than the value used in this example, each component can be used. in an amount that is from 10% less to 10% more than the value used in this example, each component can be used in an amount that is from 15% less to 15% more than the value used in this example, or each component can be used in an amount that is from 20% less to 20% more than the value used in this example. In various aspects, the values can be varied by about plus or minus 5% to 20%.

Synthesis of Labeled QAOC Reagent (6)

To a cold suspension of p-Acetyl-4-phenylurazole quaternary aminooxy adduct heptafluoro butyrate 5 (800 mg, 1.46 mmol, under argon atmosphere) a solution of tBuOCl (0.175 mL, 1.46 mmol in 7 mL of anhydrous acetonitrile) was added (2-3 min addition) dropwise while stirring. After addition is complete the reaction mixture was stirred at 0-5° C. for 30 min. Acetonitrile was removed by a rotary evaporator (vented with nitrogen) and the pink solid was washed with anhydrous EtOAc (removed by pasture pipette from top under a blanket of argon). 0.65 g (80%) of 6 was obtained as an orange-red solid after drying under vacuum. Product was stored at −40° C., free of moisture and protected from bright light. In various aspects, the values of each of the components used in this example can be increased or decreased by an amount in the range of from about 5% to about 20%, for example, each component can be used in an amount that is from 5% less to 5% more than the value used in this example, each component can be used in an amount that is from 10% less to 10% more than the value used in this example, each component can be used in an amount that is from 15% less to 15% more than the value used in this example, or each component can be used in an amount that is from 20% less to 20% more than the value used in this example. In various aspects, the values can be varied by about plus or minus 5% to 20%.

Example 2

Sample Enrichment

Volume of samples, extraction solvents and their composition, reagent solutions, extraction media amount, and molecular weight cutoff membranes types are typical.

Dried Blood Spot: A sample of dried human or animal blood (3-10 µL) on filter paper was spiked with internal standard(s) and extracted with 100 µL of ethyl acetate-hexanes, preferably with a composition of 1:1, more preferably multiple times (sonication may be necessary to enhance the extraction efficiency). The combined ethyl acetate-hexanes layers were then dried down using a centrifugal vacuum concentrator or gas flow with heat or a combination of all. To the dried sample was added 50 µL of reagent solution (2 mg/mL in acetonitrile). The sample was vortexed to mix and then incubated at room temperature for at least 30 min. Water (20 µL) was added, the sample vortexed to mix, and the sample then analyzed by LC-MSMS.

Protein Precipitation: To a sample of human or animal serum or plasma (200 µL) containing internal standard(s) was added 0.8 mL of acetonitrile. The sample was vortexed to mix and then centrifuged at 10,000×g for 5 min. The supernatant (750 µL) was removed and then dried down using a centrifugal vacuum concentrator or gas flow with heat or a combination of all. To the dried sample was added 50 µL of reagent solution (2 mg/mL in acetonitrile). The sample was vortexed to mix and then incubated at room temperature for at least 30 min. Water (20 µL) was added, the sample vortexed to mix, and the sample then analyzed by LC-MSMS.

Liquid-Liquid Extraction (LLE): A sample of human or animal serum or plasma (200 µL) containing internal standard(s) was extracted with 1 mL of ethyl acetate-hexanes, preferably a composition of 1:1, more preferably multiple times. The combined ethyl acetate-hexanes layers were then dried down using a centrifugal vacuum concentrator or gas flow with heat or a combination of all. To the dried sample was added 50 µL of reagent solution (2 mg/mL in acetonitrile). The sample was vortexed to mix and then incubated at room temperature for at least 30 min. Water (20 µL) was added, the sample vortexed to mix, and the sample then analyzed by LC-MSMS.

Solid-Liquid Extraction (SLE): A sample of human or animal serum or plasma (200 µL) containing internal standard(s) was applied on a 200 mg Diatomaceous earth media, preferably in a cartridge or a 96 well-plate or any other suitable formats, allowed to adsorb for 5-10 minute and then extracted with 1 mL of diisopropyl ether, preferably multiple times. The combined diisopropyl ether extracts were then dried down using a centrifugal vacuum concentrator or gas flow with heat or a combination of all. To the dried sample was added 50 µL of reagent solution (2 mg/mL in acetonitrile). The sample was vortexed to mix and then incubated at room temperature for at least 30 min. Water (20 µL) was added, the sample vortexed to mix, and the sample then analyzed by LC-MSMS.

Free (Unbound) Estrogens: A sample of human or animal serum or plasma (400 µL) was applied on a 30 kDa Ultra-filtration (UF) membrane or device and centrifuged at 3000-5000 g for 1 hour. The filtrate was then spiked with internal standard(s) and extracted with 1 mL of diisopropyl ether, preferably multiple times. The combined diisopropyl ether extracts were then dried down using a centrifugal vacuum concentrator or gas flow with heat or a combination of all. To the dried sample was added 50 µL of reagent solution (2 mg/mL in acetonitrile). The sample was vortexed to mix and then incubated at room temperature for at least 30 min. Water (20 µL) was added, the sample vortexed to mix, and the sample then analyzed by LC-MSMS.

Example 3

Mass Spectrometry Analysis

A sample may be analyzed using the following parameters in an LC-MSMS Analysis.
HPLC Parameters

| Column: | AAA C18 Column (C18 reversed-phase, 5 µm, 4.6 mm × 150 mm) |
|---|---|
| Temperature: | 50° C. |
| Mobile Phases: | A = $H_2O$ + 0.1% FA |
|  | B = Acetonitrile + 0.1% FA |
| Injection Volume: | 20 µL |

| Gradient: | | | | |
|---|---|---|---|---|
| Step | Total Time (min) | Flow Rate (µl/min) | A (%) | B (%) |
| 0 | 0.00 | 1000 | 70.0 | 30.0 |
| 1 | 5.00 | 1000 | 5.0 | 95.0 |
| 2 | 5.50 | 1000 | 5.0 | 95.0 |
| 3 | 6.00 | 1000 | 70.0 | 30.0 |
| 4 | 10.00 | 1000 | 70.0 | 30.0 |

The HPLC and MS parameters are typical values and are not limiting.

Example 4

Analysis of Estrogens on the API-5500 QTRP

Figure 5A:
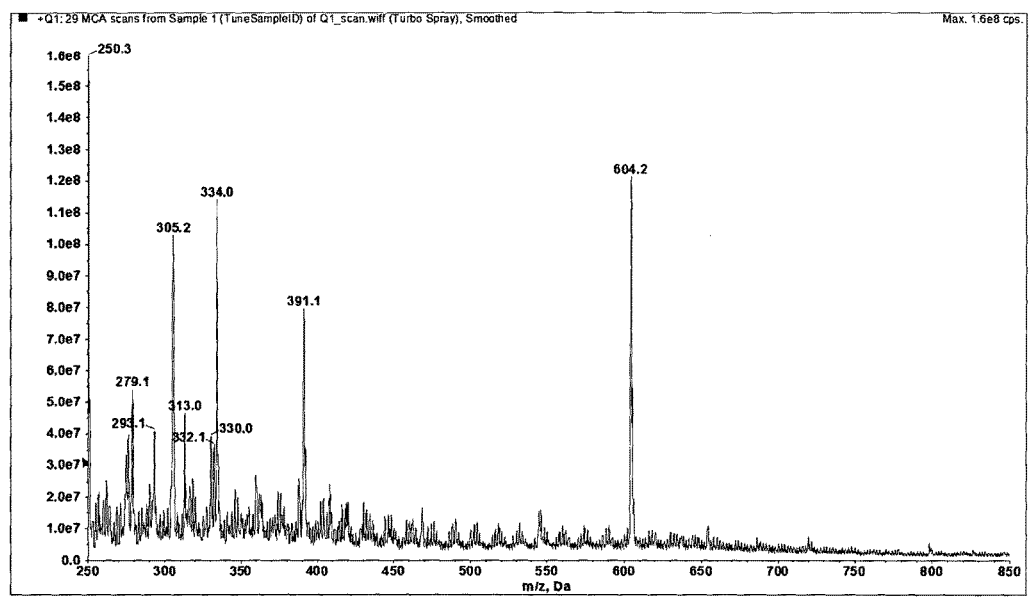
FIG. 5A is a Q1-MS-Q1 Scan of the reaction mixture shown in FIG. 3 using the API-5500 QTRP™ mass spectrometer: Expected $M^+$=604.35, Found 604.2.
Figure 5B:
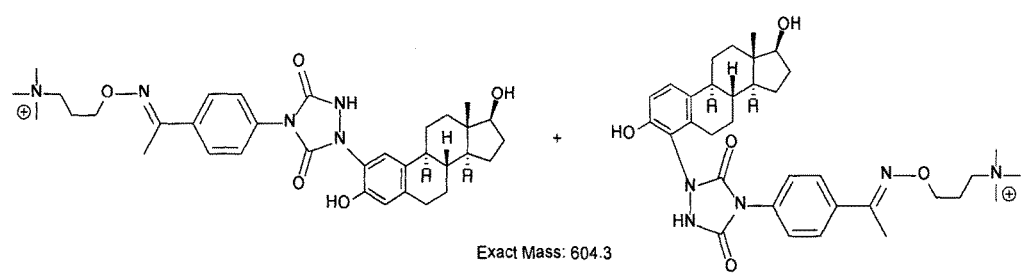
FIG. 5B shows the chemical structures of both isomeric forms of the estradiol-QAOC adduct.

Using a similar process, estradiol was reacted with the labeled QAOC of Formula I according to the mechanism shown in FIG. 4 and analyzed using a Q1-MS-Q1 scan. FIG. 5A provides a scan of the reaction mixture using the API-5500 QTRP™ mass spectrometer, made by AB SCIEX. As shown, the expected $M^+$=604.35, but was found at 604.2.

Figure 6A:
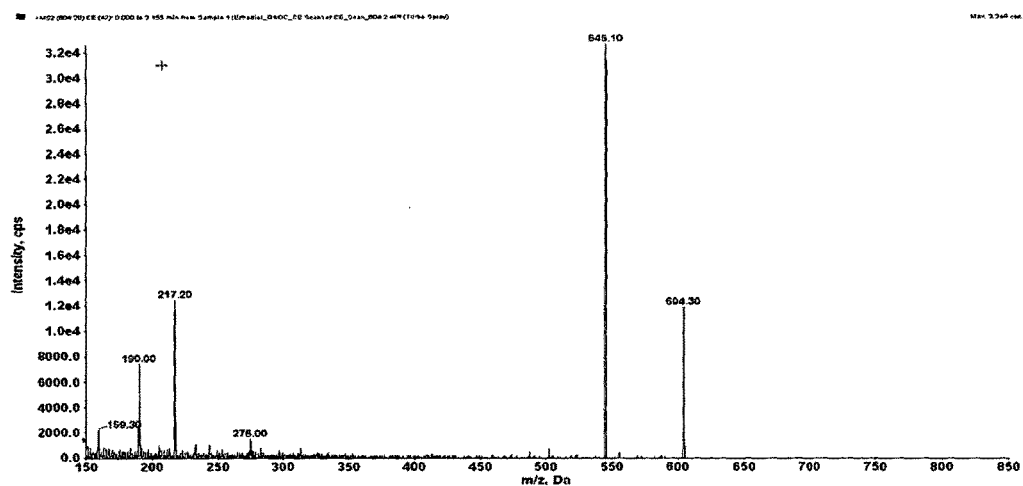
FIG. 6A shows the collision energy scan for the compounds shown in FIG. 5B at m/z=604.3 and some of the MRM fragments including neutral loss fragment at m/z=545.1.
Figure 6B:
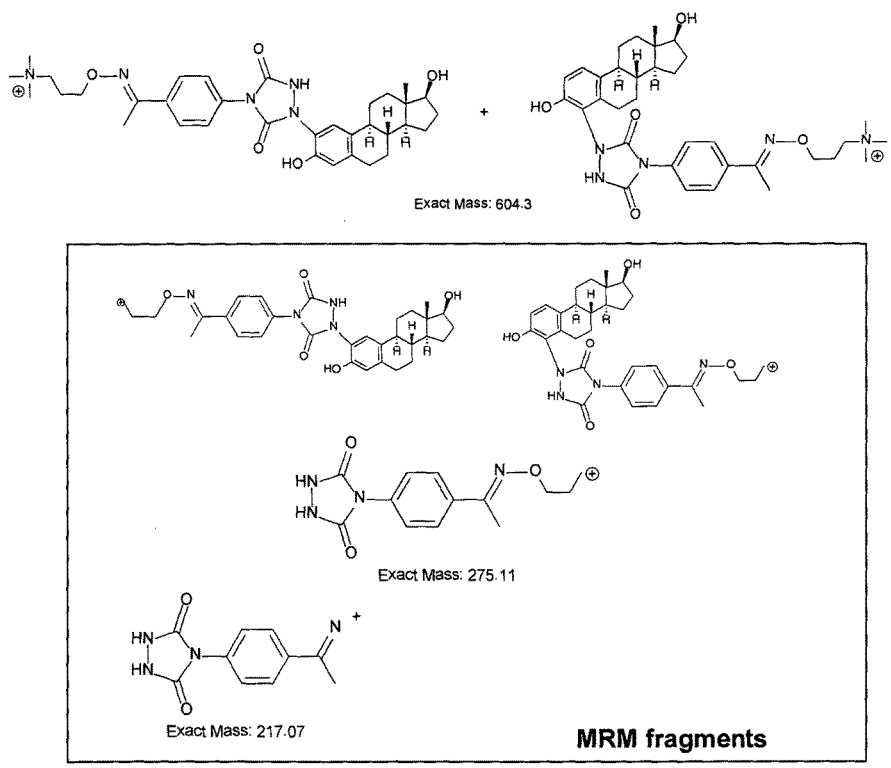
FIG. 6B shows the chemical structures of adducts of FIG. 5A as well as the MRM fragments of FIG. 6A.
Figure 7:
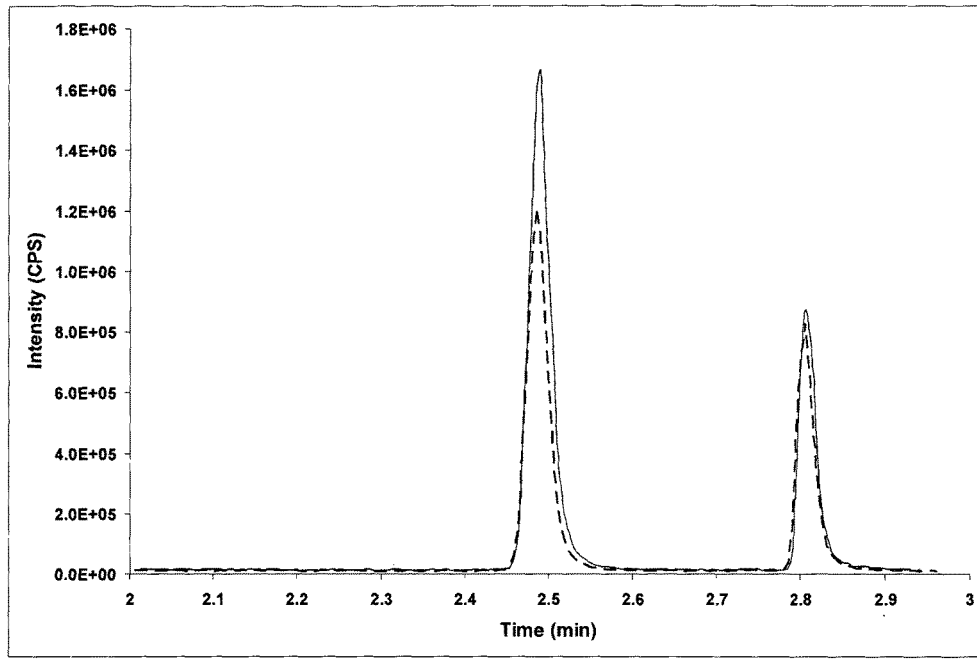
FIG. 7 shows a LC-MRM Profile of the reaction mixture of FIG. 4, showing two MRM transitions by dotted line and continuous line.

According to some embodiments, when the isobaric tag is an aminooxy MS tagging agent, the reporter signal can be subjected to further fragmentation ($MS^3$). Subjecting the reporter signal to further fragmentation can provide peaks that enable confirmatory identification of the analyte by comparing with a standard database. According to some embodiments, the eluent from the column can be subjected to Parent Daughter Ion Transition Monitoring (PDITM). This product ion at m/z 604.3 was subject to a collision energy scan and the results are shown in FIG. 6A. The parent ion as well as some of the MRM fragments including neutral loss fragment at 545.1 can be seen in FIG. 6B. This reaction mixture was then subject to a LC-MRM profile for both MRM transitions: 604.34→545.1 and 604.3→217.2, which is shown in FIG. 7 (dotted and continuous traces). The reaction mixture was provided in an Acetonitrile-Water (0.1% Formic acid) gradient 54→95% B in 8 min, Water's Acquity C8 UPLC column, 0.7 mL/min, 5 µL injection, 40° C. column compartment.

Example 5

Analysis of Estrogens on the 3200QTRAP

Estrone, estradiol, and estriol were each enriched and reacted with the labeled QAOC reagent of Formula I and the fragmentation patterns of the product ions have been determined. The MSMS parameters, using a 3200 QTRAP instrument were:

| Compound | Q1 | Q3 | time (msec) | DP | EP | CE | CXP |
|---|---|---|---|---|---|---|---|
| Estrone (E1) | 602.4 | 543.3 | 50 | 46 | 4.0 | 29 | 6 |
| Estradiol (E2) | 604.4 | 545.3 | 50 | 46 | 7.0 | 31 | 6 |
| Estriol (E3) | 620.4 | 561.3 | 50 | 51 | 6.5 | 30 | 6 |

Figure 8:
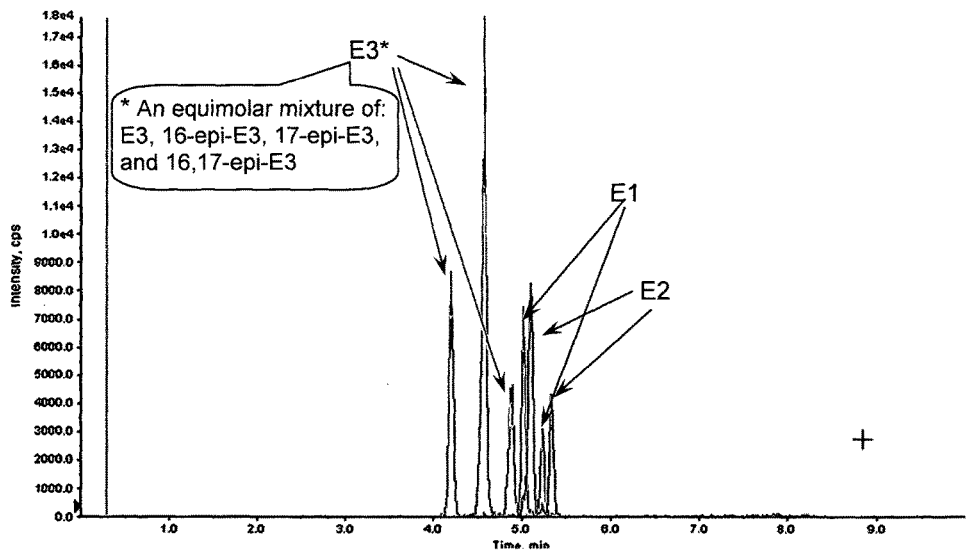
FIG. 8 provides a LC-MRM profile of a reaction comprising estrone (E1), estradiol (E2), and estriols (E3), labeled with the QAOC reagent of FIG. 1.

The source/gas parameters used were:
CUR: 10.00
IS: 5000.00
TEM: 500.00
GS1: 20.00
GS2: 20.00
ihe: ON
CAD: High FIG. 8 provides a LC-MRM profile of a reaction comprising estrone, estradiol, and estriols, labeled with the QAOC reagent of FIG. 1.

The section headings used herein are for organizational purposes only and are not to be construed as limiting the subject matter described in any way.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

While the above description provides examples and specific details of various embodiments, it will be appreciated that some features and/or functions of the described embodiments admit to modification without departing from the scope of the described embodiments. The above description is intended to be illustrative of the invention, the scope of which is limited only by the language of the claims appended hereto. Other embodiments of the present teachings will be apparent to those skilled in the art from consideration of the present specification and practice of the present teachings disclosed herein. It is intended that the present specification and examples be considered exemplary only.

The invention claimed is:

1. A method for mass spectrometric analysis of a sample, comprising the steps:
    treating the sample with a QAOC reagent so as to label at least one phenolic OH analyte in the sample to create a phenolic QAOC adduct; and
    analyzing the phenolic QAOC adduct using a mass spectrometer;
wherein said QAOC reagent has the formula:

wherein $R_1$ is

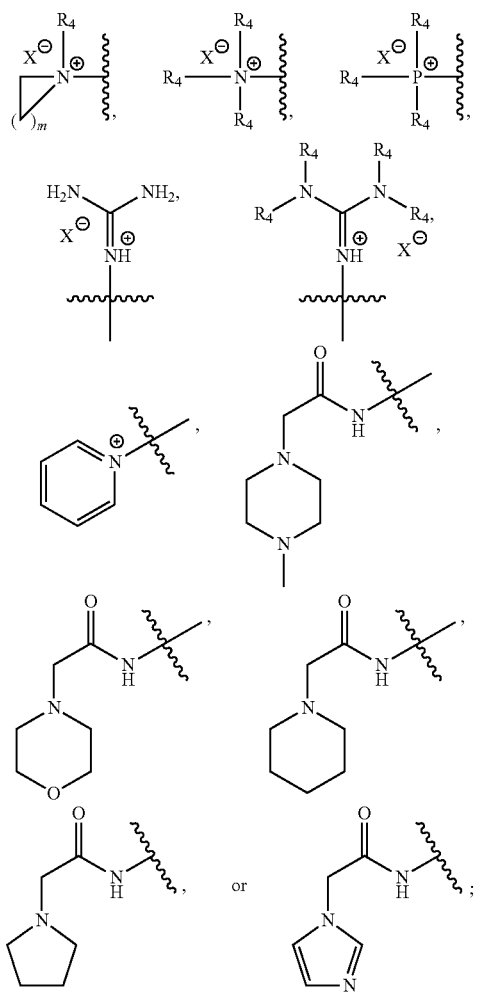

$R_2$ is a cyclic, branched or straight chain, substituted or unsubstituted $C_1$-$C_{18}$ alkyl, $C_1$-$C_{18}$ alkene, or $C_1$-$C_{18}$ alkyne or a substituted or unsubstituted aromatic group;

$R_3$ is absent or is one or more substituents that are the same or different, which is a cyclic, branched or straight chain $C_1$-$C_{18}$ alkyl, $C_1$-$C_{18}$ alkene, or $C_1$-$C_{18}$ alkyne; halogen; —$NO_2$; a substituted or unsubstituted aromatic group; a protected or unprotected amino, acyl, carboxylic acid, or thiol group; —$SO_3H$, —$PO_4^-$, thioether, ether, epoxide, thio-epoxide, azide or aziridine;

each $R_4$ is independently H or a cyclic, branched or straight chain $C_1$-$C_{18}$ alkyl, $C_1$-$C_{18}$ alkene, or $C_1$-$C_{18}$ alkyne;

m is an integer between 1 and 20;

X is an anion;

L1 and L2 are independently bonds or linkers; and

Ar is bond, an aryl or heteroaryl group.

2. The method of claim 1, wherein $R_2$ is methyl or ethyl and $R_3$ is absent;

and/or L1 and L2 are independently a bond, a peptide, an oligomer, PEG, or a $C_1$-$C_{20}$ alkylene chain.

3. The method of claim 1, wherein said at least one phenolic OH analyte is a steroid and optionally wherein said steroid is an estrogen compound selected from the group consisting of estriol, 16-epiestriol, 17-epiestriol, and 16,17-epiestriol, estrone (E1), estrone sulfate (E1s), 17α-estradiol (E2a), 17β-estradiol (E2b), estradiol sulfate (E2s), equilin (EQ), 17α-dihydroequilin (EQa), 17β-dihydroequilin (EQb), Eqilenin (EN), 17α-dihydroequilenin (ENa) 17β-dihydroequilenin (ENb), Δ8,9-dehydroestrone (dE1), Δ8,9-dehydroestrone sulfate (dE1s).

4. The method of claim 1, wherein the QAOC reagent is generated by reacting a compound having the structure:

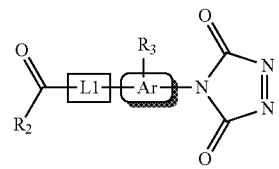

with an aminooxy tag to form a tagged QAOC reagent having the structure:

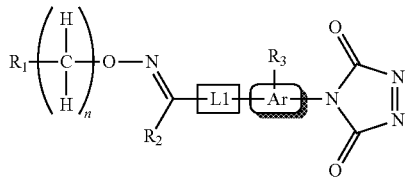

wherein n is an integer between 1 and 20.

5. The method of claim 4, wherein $R_2$ is methyl or ethyl, $R_3$ is absent, $R_4$ is methyl, m is an integer between 1 and 5, and X is a perfluorocarboxylate; and/or wherein L1 is a bond, Ar is a phenyl group, and n is an integer between 1 and 8.

6. The method of claim 4, wherein the tagged QAOC reagent has the structure:

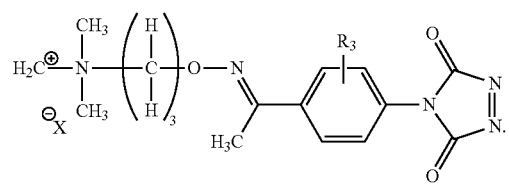

7. A method for mass spectrometric analysis of a sample, comprising the steps:
   treating the sample with a PTAD reagent so as to react at least one phenolic OH analyte in the sample to create a PTAD adduct;
   labelling the PTAD adduct with a aminoxy tagging agent to form a tagged adduct and
   analyzing the tagged adduct using a mass spectrometer;
   wherein the PTAD reagent has the structure of:

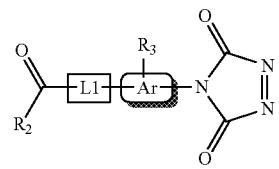

R₂ is a cyclic, branched or straight chain, substituted or unsubstituted $C_1$-$C_{18}$ alkyl, $C_1$-$C_{18}$ alkene, or $C_1$-$C_{18}$ alkyne or a substituted or unsubstituted aromatic group;

R₃ is absent or is one or more substituents that are the same or different, which is a cyclic, branched or straight chain $C_1$-$C_{18}$ alkyl, $C_1$-$C_{18}$ alkene, or $C_1$-$C_{18}$ alkyne; halogen; (e.g., Cl, Br, I, or F); —NO₂, a substituted or unsubstituted aromatic (aryl) group; a protected or unprotected amino, acyl, carboxylic acid, or thiol group; —SO₃H, —PO₄⁻, thioether, ether, epoxide, thio-epoxide, azide or aziridine;

Ar is a bond, an aryl group, or a heteroaryl group; and

L1 is a bond or linker;

and wherein the aminoxy tanning anent has the structure of:

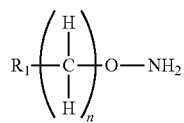

wherein n is from 1 to 20, and R₁ is a quaternary amine or a substituent having the structure:

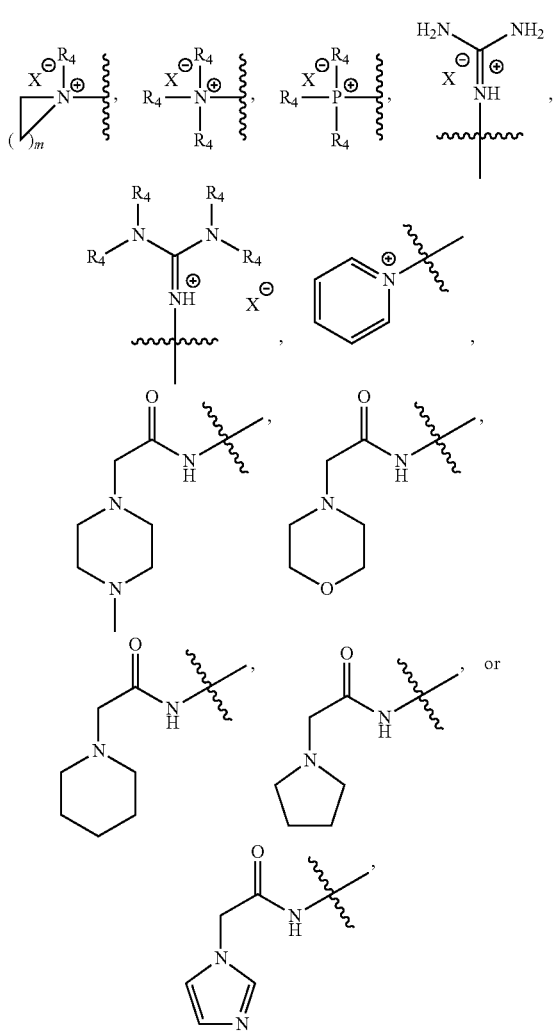

wherein each R₄ is independently H or a cyclic, branched or straight chain $C_1$-$C_{18}$ alkyl, $C_1$-$C_{18}$ alkene, or $C_1$-$C_{18}$ alkyne;

m is an integer between 1 and 20, and X is an anion;

and wherein the tagged adduct has the following substructure:

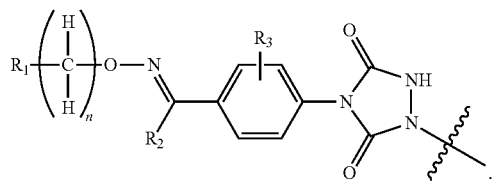

8. The method of claim 7, wherein R₂ is methyl or ethyl, R₃ is absent, R₄ is methyl, n is an integer between 2 and 4, and X is a perfluorocarboxylate.

9. The method of claim 1 or 7, wherein X is CF₃COO—, CF₃CF₂COO—, CF₃CF₂CF₂COO—, CF₃SO₃COO—, (C₆H₅)₄B—.

10. The method of claim 7, wherein the tagged adduct has the substructure

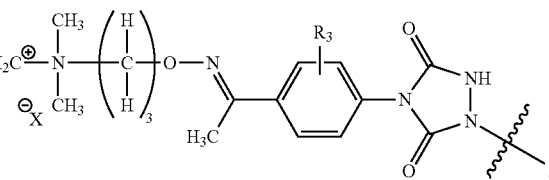

11. The method of claim 1, wherein the sample is a biological sample and wherein the biological sample is optionally selected from blood, plasma, serum, urine, or saliva, cerebral fluid, tissue, hair, body fluids.

12. The method of claim 1, wherein said at least one phenolic OH analyte is a steroid, and wherein said method further comprises:
(a) creating a set of calibration matrices by spiking known volumes of one or more steroid depleted biological sample with known amount of one or more steroid internal standards and one or more steroids having known incremental concentrations;
(b) treating the calibration matrices obtained from step (a) with the QAOC reagent utilized to label the at least one phenolic OH analyte that is a steroid in the sample or an isotopic variant thereof, so as to label at least one of the one or more steroids having known incremental concentrations and corresponding internal standard;
(c) analyzing the calibration matrices of step (b) using LC-MSMS;
(d) generating a calibration curve using the data obtained from the analysis of step (c);
(e) spiking said phenolic OH analyte that is a steroid in the sample with known amount of one or more steroid internal standard; and
(f) using said calibration curve to estimate the amount of said at least one phenolic OH analyte which is a steroid in sample.

13. The method of claim 12, wherein analyzing the phenolic QAOC adduct or the calibration matrices further comprises parent daughter ion transition monitoring (PDITM) of the phenolic-QAOC adduct using a triple quadrupole MS platform.

14. The method of claim 1, wherein said at least one phenolic OH analyte is a steroid, and
wherein said method further comprises:
(a) providing an internal or external standard comprising a known concentration of a steroid analyte comprising a phenolic OH;
(b) treating said standard with said QAOC reagent to form a standard adduct;
(c) analyzing the standard adduct using mass spectrometry;
(d) estimating the amount of said at least one phenolic OH analyte which is a steroid in said sample and optionally wherein analyzing the phenolic-QAOC adduct and analyzing the standard adduct comprises parent daughter ion transition monitoring (PDITM) of the phenolic-AOC adduct and the standard adduct using a triple quadrupole MS platform.

15. The method of claim 1, wherein at least two phenolic OH analytes and optionally four phenolic OH analytes are measured simultaneously.

16. The method of claim 1, further comprising the step of reacting the phenolic-OH analyte with one or more isotopic variants of the QAOC reagent to form at least one phenolic OH internal standard.

17. The method of claim 1, further comprising simultaneously quantitating one or more Vitamin D-QAOC and phenolic QAOC adducts, wherein the Vitamin D-QAOC is made by reacting Vitamin D with the QAOC reagent utilized to label the at least one phenolic OH analyte in the sample to form the phenolic QAOC adduct.

18. A kit for use in mass spectrometric analysis of a sample comprising
a QAOC reagent and standards comprising a known concentrations of a steroid analytes comprising phenolic OH, in a package and
wherein the QAOC reagent has the structure:

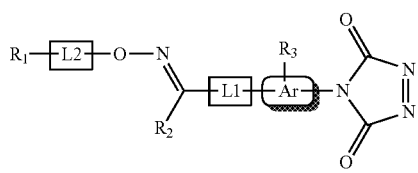

wherein $R_1$ is

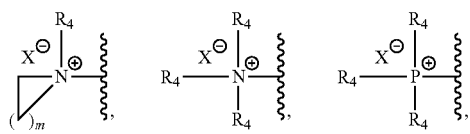

-continued

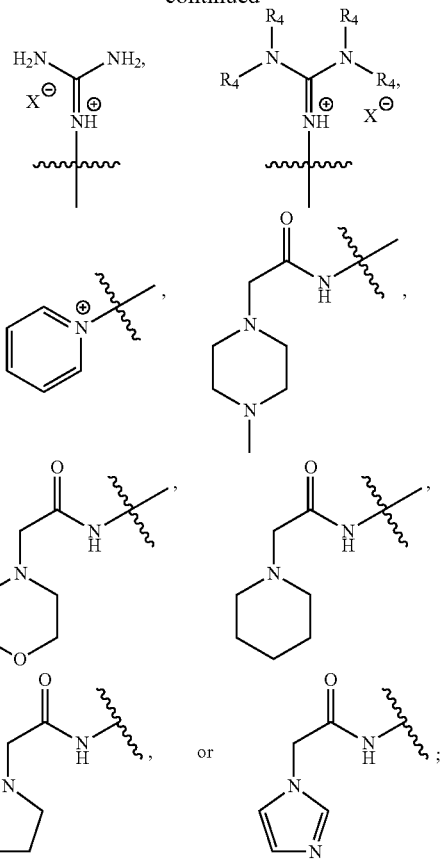

$R_2$ is a cyclic, branched or straight chain, substituted or unsubstituted $C_1$-$C_{18}$ alkyl, $C_1$-$C_{18}$ alkene, or $C_1$-$C_{18}$ alkyne or a substituted or unsubstituted aromatic group;

$R_3$ is absent or is one or more substituents that are the same or different, which is a cyclic, branched or straight chain $C_1$-$C_{18}$ alkyl, $C_1$-$C_{18}$ alkene, or $C_1$-$C_{18}$ alkyne; halogen; —$NO_2$; a substituted or unsubstituted aromatic group; a protected or unprotected amino, acyl, carboxylic acid, or thiol group; —$SO_3H$, —$PO_4^-$, thioether, ether, epoxide, thio-epoxide, azide or aziridine;

each $R_4$ is independently H or a cyclic, branched or straight chain $C_1$-$C_{18}$ alkyl, $C_1$-$C_{18}$ alkene, or $C_1$-$C_{18}$ alkyne;

m is an integer between 1 and 20;

X is an anion;

L1 and L2 are independently bonds or linkers; and

Ar is bond, an aryl or heteroaryl group.

* * * * *